United States Patent [19]
Weinstock

[11] Patent Number: 5,656,650
[45] Date of Patent: Aug. 12, 1997

[54] ANGIOTENSIN II RECEPTOR BLOCKING COMPOSITIONS

[75] Inventor: Joseph Weinstock, Phoenixville, Pa.

[73] Assignee: SmithKline Beecham Corp.

[21] Appl. No.: 444,121

[22] Filed: May 18, 1995

Related U.S. Application Data

[63] Continuation of Ser. No. 75,535, Jun. 10, 1992, which is a continuation-in-part of Ser. No. 628,807, Dec. 14, 1990, abandoned.

[51] Int. Cl.⁶ ................................................. A61K 31/415
[52] U.S. Cl. .............................................. 514/396; 514/397
[58] Field of Search ..................................... 514/396, 397

[56] References Cited

U.S. PATENT DOCUMENTS 5,177,096  1/1993  Keenan et al. ............................ 514/381
5,312,828  5/1994  Finkelstein et al. ..................... 514/381

FOREIGN PATENT DOCUMENTS 0 324377  7/1989  European Pat. Off. .
0 403 159  12/1990  European Pat. Off. .

*Primary Examiner*—Joseph Conrad
*Attorney, Agent, or Firm*—Mary E. McCarthy; Stephen Venetianer; Edward T. Lentz

[57] ABSTRACT

This invention relates to pharmaceutical compositions comprising a pharmaceutically acceptable carrier, an angiotensin II receptor antagonist and a second agent selected from a diuretic, a calcium channel blocker, a β-adrenoceptor blocker, a renin inhibitor, or an angiotensin converting enzyme inhibitor and a method of treating hypertension.

20 Claims, 1 Drawing Sheet

Effect of HCTZ and Compound A on Mean Arterial Pressure

Effect of HCTZ and Compound A on Mean Arterial Pressure

Figure 1

ANGIOTENSIN II RECEPTOR BLOCKING COMPOSITIONS

This is a continuation of application Ser. No. 08/075,535, filed Jun. 10, 1993, which application is a continuation-in-part of U.S. Ser. No. 07/628,807, filed Dec. 14, 1990 now abandoned.

FIELD OF INVENTION

This invention relates to pharmaceutical compositions comprising angiotensin II receptor antagonists, combined with other agents, particularly diuretics, calcium channel blockers, β-adrenoceptor blockers, renin inhibitors, or angiotensin converting enzyme inhibitors. The invention also relates to a method of treating hypertension by administering said compositions to a subject in need thereof or by stepwise combined therapy.

BACKGROUND OF THE INVENTION

The class of peptide pressor hormone known as angiotensin is responsible for a vasopressor action that is implicated in the etiology of hypertension in man. Inappropriate activity of the renin-angiotensin systems appears to be a key element in essential hypertension, congestive heart failure and in some forms of renal disease. In addition to a direct action on arteries and arterioles, angiotensin II (AII), being one of the most potent endogenous vasoconstrictors known, exerts stimulation on the release of aldosterone from the adrenal cortex. Therefore, the renin-angiotensin system, by virtue of its participation in the control of renal sodium handling, plays an important role in cardiovascular hemeostasis.

Interruption of the renin-angiotensin system with converting enzyme inhibitors, such as captopril, has proved to be clinically useful in the treatment of hypertension and congestive heart failure (Abrams, W. B., et al., (1984), *Federation Proc.*, 43, 1314). The most direct approach towards inhibition of the renin-angiotensin system would block the action of AII at the receptor. Compelling evidence suggests that AII also contributes to renal vasoconstriction and sodium retention that is characteristic of a number of disorders such as heart failure, cirrhosis and complications of pregnancy (Hollenberg, N. K., (1984), *J. Cardiovas. Pharmacol.*, 6, S176). In addition, recent animal studies suggest that inhibition of the renin-angiotensin system may be beneficial in halting or slowing the progression of chronic renal failure (Anderson, S., et al., (1985), *J. Clin. Invest.*, 76, 612). Also, a recent patent application (South African Patent Application No. 87/01,653) claims that AII antagonists are useful as agents for reducing and controlling elevated intraocular pressure, especially glaucoma, in mammals.

The compounds described herein inhibit, block and antagonize the action of the hormone AII, and are therefore useful in regulating and moderating angiotensin induced hypertension, congestive heart failure, renal failure and other disorders attributed to the actions of AII. When the AII receptor blocking compounds are administered to mammals, the elevated blood pressure due to AII is reduced and other manifestations based on AII intercession are minimized and controlled. These compounds are also expected to exhibit diuretic activity.

One of the drawbacks of current antihypertensive therapy is that cardiovascular morbidity and mortality is higher in treated hypertensive patients than in normotensive subjects of the same age, sex, and from the same population [Isles, et al., *J. Hypertension*, 4, 141 (1986) and Samuelsson, O., *Acta Med. Scand*, Suppl. 702, 1 (1985)]. A possible explanation for this result is that arterial pressure in treated hypertensive patients is significantly higher than in matched normotensive subjects. Thus, it would appear that a therapeutic goal for the treatment of hypertension would be to obtain normotensive blood pressure levels in treated hypertensive patients [Hansson, L., *Br. J. Clin. Pharmacol.*, 23, 15S (1987)]. To achieve this goal, the instant invention involves the administration of an agiotensin II receptor blocking compound in combination with a second agent, such as a diuretic, a calcium channel blocker, a β-adrenoceptor blocker, a renin inhibitor, or an angiotensin converting enzyme inhibitor.

According to the present invention there are provided pharmaceutical compositions comprising a pharmaceutically acceptable carrier in association with a diuretic and an angiotensin II blocking agent of formula (I)–(IX), hereinbelow.

Substituted imidazoles of the formula (I) are disclosed in U.S. application Ser. No. 07/746,262, filed Aug. 14, 1991:

in which:

$R^1$ is adamantyl, phenyl, biphenyl, or naphthyl, with each aryl group being unsubstituted or substituted by one to three substituents selected from Cl, Br, F, I, $C_1-C_6$alkyl, nitro, $A-CO_2R^7$, tetrazol-5-yl, $C_1-C_6$alkoxy, hydroxy, $SC_1-C_6$alkyl, $SO_2NHR^7$, $NHSO_2R^7$, $SO_3H$, $CONR^7R^7$, CN, $SO_2C_1-C_6$alkyl, $NHSO_2R^7$, $PO(OR^7)_2$, $NR^7R^7$, $NR^7COH$, $NR^7COC_1-C_6$alkyl, $NR^7CON(R^7)_2$, $NR^7COW$, W, or $SO_2W$;

m is 0–4;

$R^2$ is $C_2-C_{10}$alkyl, $C_3-C_{10}$alkenyl, $C_3-C_{10}$alkynyl, $C_3-C_6$cycloalkyl, or $(CH_2)_{0-8}$phenyl unsubstituted or substituted by one to three substituents selected from $C_1-C_6$alkyl, nitro, Cl, Br, F, I, hydroxy, $C_1-C_6$alkoxy, $NR^7R^7$, $CO_2R^7$, CN, $CONR^7R^7$, W, tetrazol-5-yl, $NR^7COC_1-C_6$alkyl, $NR^7COW$, $SC_1-C_6$alkyl, $SO_2W$, or $SO_2C_1-C_6$alkyl;

X is a single bond, S, $NR^7$, or O;

$R^3$ is hydrogen, Cl, Br, F, I, CHO, hydroxymethyl, $COOR^7$, $CONR^7R^7$, $NO_2$, W, CN, $NR^7R^7$, or phenyl;

$R^4$ and $R^5$ are independently hydrogen, $C_1-C_6$alkyl, thienyl-Y-, furyl-Y-, pyrazolyl-Y-, imidazolyl-Y-, pyrrolyl-Y-, triazolyl-Y-, oxazolyl-Y-, isoxazolyl-Y-, thiazolyl-Y-, pyridyl-Y-, or tetrazolyl-Y-, except that $R^4$ and $R^5$ are not both selected from hydrogen and $C_1-C_6$alkyl and each heterocyclic ring is unsubstituted or substituted by $C_1-C_6$alkyl, $C_1-C_6$alkoxy, Cl, Br, F, I, $NR^7R^7$, $CO_2R^7$, $SO_2NHR^7$, $SO_3H$, or $CONR^7R^7$, OH, $NO_2$, W, $SO_2W$, $SC_1-C_6$alkyl, $SO_2C_1-C_6$alkyl, $NR^7COH$, $NR^7COW$, or $NR^7COC_1-C_6$alkyl;

Y is a single bond, O, S, or $C_1-C_6$alkyl which is straight or branched or optionally substituted by phenyl or benzyl, wherein each of the aryl groups is unsubstituted or substituted by halo, $NO_2$, $CF_3$, $C_1-C_6$alkyl, $C_1-C_6$alkoxy, CN, or $CO_2R^7$;

$R^6$ is $-Z-COOR^8$ or $-Z-CONR^7R^7$;

Z is a single bond, vinyl, $-CH_2-O-CH_2-$, methylene optionally substituted by $C_1-C_6$alkyl, one or two benzyl groups, thienylmethyl, or furylmethyl, or $-C(O)NHCHR^9-$, wherein $R^9$ is H, $C_1-C_6$alkyl, phenyl, benzyl, thienylmethyl, or furylmethyl;

W is $C_nF_{2n+1}$, $C_nF_{2n+1}$, wherein n is 1–3;

A is —$(CH_2)_m$—, —CH=CH—, —$O(CH_2)_n$—, or —$S(CH_2)_n$—;

each $R^7$ independently is hydrogen, $C_1$-$C_6$alkyl, or $(CH_2)_m$phenyl, wherein m is 0–4; and $R^8$ is hydrogen, $C_1$-$C_6$alkyl, or 2-di($C_1$-$C_6$alkyl)amino-2-oxoethyl; or a pharmaceutically acceptable salt thereof.

Preferred compounds included within the scope of formula (I) are:

(E)-3-[2-n-butyl-1-{4-carboxyphenyl)methyl}-1H-imidazol-5-yl]-2-(2-thienyl)methyl-2-propenoic acid, (E)-3-[2-n-butyl-1-{(4-carboxynaphth-1-yl)methyl}-1H-imidazol-5-yl]-2-(2-thienyl)methyl-2-propenoic acid, (E)-3-[2-n-butyl-1-{2-chloro-4-carboxyphenyl)methyl}-1H-imidazol-5-yl]-2-(2-thienyl)methyl-2-propenoic acid, and

(E)-3-[2-n-butyl-1-{4-carboxy-2,3-dichlorophenyl)methyl}-1H-imidazol-5-yl]-2-(2-thienyl)methyl-2-propenoic acid; or a pharmaceutically acceptable salt thereof.

Particularly preferred are (E)-3-[2-n-butyl-1-{(4-carboxyphenyl)methyl}-1H-imidazol-5-yl]-2-(2-thienyl)methyl-2-propenoic acid and (E)-3-[2-n-butyl-1-{(4-carboxynaphth-1-yl)methyl}-1H-imidazol-5-yl]-2-(2-thienyl)methyl-2-propenoic acid, or a pharmaceutically acceptable salt thereof.

The most preferred compound of this invention is (E)-3-[2-n-butyl-1-{(4-carboxyphenyl)methyl]-1 H-imidazolyl-5-yl]-2-(2-thienyl)methyl-2-propenoic acid methanesulfonate.

Compounds of formula (I) are prepared following the methods described in European Patent Publication Number EP 0 403 159, published on Dec. 19, 1990.

Substituted imidazoles of the formula (II) are disclosed U.S. application Ser. No. 07/747,024, filed Aug. 14, 1991:

(II)

in which:

$R^1$ is adamantyl, phenyl, biphenyl, or naphthyl, with each aryl group being unsubstituted or substituted by one to three substituents selected from Cl, Br, F, I, $C_1$-$C_6$alkyl, nitro, A—$CO_2R^7$, tetrazol-5-yl, $C_1$-$C_6$alkoxy, hydroxy, $SC_1$-$C_6$alkyl, $SO_2NHR^7$, $NHSO_2R^7$, $SO_3H$, $CONR^7R^7$, CN, $SO_2C_1$-$C_6$alkyl, $NHSO_2R^7$, $PO(OR^7)_2$, $NR^7R^7$, $NR^7COH$, $NR^7COC_1$-$C_6$alkyl, $NR^7CON(R^7)_2$, $NR^7COW$, W, $SO_2W$; m is 0–4;

$R^2$ is $C_2$-$C_{10}$alkyl, $C_3$-$C_{10}$alkenyl, $C_3$-$C_{10}$alkynyl, $C_3$-$C_6$cycloalkyl, or $(CH_2)_{0-8}$phenyl unsubstituted or substituted by one to three substituents selected from $C_1$-$C_6$alkyl, nitro, Cl, Br, F, I, hydroxy, $C_1$-$C_6$alkoxy, $NR^7R^7$, $CO_2R^7$, CN, $CONR^7R^7$, W, tetrazol-5-yl, $NR^7COC_1$-$C_6$alkyl, $NR^7COW$, $SC_1$-$C_6$alkyl, $SO_2W$, or $SO_2C_1$-$C_6$alkyl;

X is a single bond, S, $NR^7$, or O;

$R^3$ is hydrogen, Cl, Br, F, I, CHO, hydroxymethyl, $COOR^7$, $CONR^7R^7$, $NO_2$, W, CN, $NR^7R^7$, or phenyl;

$R^4$ and $R^5$ are independently hydrogen, $C_1$-$C_6$alkyl, phenyl-Y-, naphthyl-Y-, or biphenyl-Y-, wherein the aryl groups are unsubstituted or substituted by one to three substituents selected from Cl, Br, F, I, $C_1$-$C_6$alkoxy, hydroxy, $CO_2R^7$, CN, $NO_2$, tetrazol-5-yl, $SO_3H$, $CF_3$, $CONR^7R^7$, $SO_2NHR^7$, $C_1$-$C_6$alkyl, or $NR^7R^7$, or by methylenedioxy, phenoxy or phenyl, except that $R^4$ and $R^5$ are not both selected from hydrogen;

Y is a single bond, O, S, or $C_1$-$C_6$alkyl which is straight or branched or optionally substituted by phenyl or benzyl, wherein each of the aryl groups is unsubstituted or substituted by halo, $NO_2$, $CF_3$, $C_1$-$C_4$alkyl, $C_1$-$C_4$alkoxy, CN, or $CO_2R^7$;

$R^6$ is —Z—$COOR^8$ or —Z—$CONR^7R^7$;

Z is a single bond, vinyl, —$CH_2$—O—$CH_2$—, methylene optionally substituted by $C_1$-$C_4$alkyl, one or two benzyl groups, thienylmethyl, or furylmethyl, or —C(O)NHCHR$^9$—, wherein $R^9$ is H, $C_1$-$C_4$alkyl, phenyl, benzyl, thienylmethyl, or furylmethyl;

each $R^7$ independently is hydrogen, $C_1$-$C_4$alkyl, or $(CH_2)_m$phenyl, wherein m is 0–4; and $R^8$ is hydrogen, $C_1$-$C_6$alkyl, or 2-di($C_1$-$C_4$alkyl)-amino-2-oxoethyl; or $R^5$ and $R^6$ are both hydrogen, $R^4$ is —Z—$COOR^8$ and Z is other than a single bond; or a pharmaceutically acceptable salt thereof.

Compounds of formula (II) are prepared following the methods described in European Publication Number EP 0 403 158, published on Dec. 19, 1990.

Preferred compounds included within the scope of formula (II) are:

(E)-3-[2-n-butyl-1-{(2-chlorophenyl)methyl}-1H-imidazol-5-yl]-2-(3,4-methylenedioxyphenyl)methyl-2-propenoic acid, (E)-3-[2-n-butyl-1-{(4-carboxyphenyl)methyl}-1H-imidazol-5-yl]-2-n-butyl-2-propenoic acid, and (E)-3-[2-n-butyl-1-{(4-carboxyphenyl)methyl}-1H-imidazol-5-yl]-2-benzyl-2-propenoic acid; or a pharmaceutically acceptable salt thereof.

Substituted imidazoles of the formula (III) are disclosed in U.S. application Ser. No. 07/590,207, filed Sep. 28, 1990:

(III)

in which:

$R^1$ is adamantylmethyl, or phenyl, biphenyl, or naphthyl, with each aryl group being unsubstituted or substituted by one to three substituents selected from Cl, Br, F, I, $C_1$-$C_6$alkyl, nitro, $CO_2R^7$, $C_1$-$C_6$alkoxy, hydroxy, $SC_1$-$C_6$alkyl, $SO_2C_1$-$C_6$alkyl, tetrazol-5-yl, $SO_2NHR^7$, $NHSO_2R^7$, $SO_3H$, $PO(OR^7)_2$, $CONR^7R^7$, CN, $NR^7R^7$, $NR^7COH$, $NR^7COC_1$-$C_6$alkyl, $NR^7CON(R^7)_2$, $NR^7COW$, $SO_2W$, or W; $R^2$ is $C_2$-$C_{10}$alkyl, $C_3$-$C_{10}$alkenyl, $(CH_2)_{0-8}$-$C_3$-$C_6$cycloalkyl, or $(CH_2)_{0-8}$phenyl unsubstituted or substituted by one to three substituents selected from $C_1$-$C_6$alkyl, nitro, Cl, Br, F, I, hydroxy, $C_1$-$C_6$alkoxy, $NR^7R^7$, $CO_2R^7$, CN, $CONR^7R^7$, W, $NR^7COH$, $NR^7COC_1$-$C_6$alkyl, $NR^7COW$, $SO_2W$, $SO_2C_1$-$C_6$alkyl, or $SC_1$-$C_6$alkyl;

X is a single bond, S, or O;

m is 0–4;

$R^3$ is hydrogen, Cl, Br, F, I, CHO, hydroxymethyl, $C_1$-$C_6$alkyl, $NR^7R^7$, $CO_2R^7$, $CONR^7R^7$, $NO_2$, CN, phenyl, or W;

$R^4$ and $R^5$ are each independently hydrogen, $C_1$-$C_8$alkyl, $C_3$-$C_6$cycloalkyl, thienyl-Y-, furyl-Y-, pyrazolyl-Y-, imidazolyl-Y-, thiazolyl-Y-, pyridyl-Y-, tetrazolyl-Y-, pyrrolyl-Y-, triazolyl-Y-, oxazolyl-Y-, isoxazolyl-Y-, or phenyl-Y-, with each aryl or heteroaryl group being unsubstituted or substituted by $C_1$-$C_6$alkyl, $C_1$-$C_6$alkoxy, Cl, Br, F, I, $NR^7R^7$, $CO_2R^7$, $SO_2NHR^7$, $SO_3H$, OH, $NO_2$, $CONR^7R^7$, W, $SO_2C_1$-$C_6$alkyl, $SO_2W$, $SC_1$-$C_6$alkyl, $NR^7COH$, $NR^7COW$, or $NR^7COC_1$-$C_6$alkyl;

Y is $C_1$-$C_6$alkyl which is straight or branched or a single bond;

$R^6$ is Z-tetrazol-5-yl;

Z is a single bond, vinyl, or methylene unsubstituted or substituted by $C_1$-$C_4$alkyl, one or two benzyl groups, thienylmethyl, or furylmethyl;

W is $C_nF_{2n+1}$, wherein n is 1–4; and each $R^7$ independently is hydrogen or $C_1$-$C_6$alkyl;

or a pharmaceutically acceptable salt thereof.

Preferred compounds included within the scope of formula (III) are:

- (E)-1-[2-n-butyl-1-{(4-carboxyphenyl)methyl}-1H-imidazol-5-yl]-2-(1H-tetrazol-5-yl)-3-(2-thien-yl) -1-propene, (E)-1-[2-n-butyl-1-{(4-(1H-tetrazol-5-yl)phenyl)methyl}-1H-imidazol-5-yl]-2-(1H-tetrazol-5-yl) -3-(2-thienyl)-1-propene, and
- (E)-1-[2-n-butyl-1-{(2-chlorophenyl)methyl}-1H-imidazol-5-yl]-2-(1H-tetrazol-5-yl)-3-(2-thienyl)-1-propene; or a pharmaceutically acceptable salt thereof.

Compounds of formula (III) are prepared following the methods described in European Publication Number EP 0 425 211, published on May 2, 1991.

Substituted imidazoles of the formula (IV) are disclosed in U.S. application Ser. No. 07/590,206, filed Sep. 28, 1990:

$$R-(CH_2)_n \quad R^3 \; R^4 \quad (IV)$$
$$R^1X-\underset{N}{\underset{\|}{\diagdown}}\underset{R^2}{\diagup}(CH_2)_n-N-CR^5$$
$$(CH_2)_nR^6$$

in which:

R is adamantylmethyl, or phenyl, biphenyl, or naphthyl, with each aryl group being unsubstituted or substituted by one to three substituents selected from Cl, Br, F, I, $C_1$-$C_6$alkyl, nitro, $CO_2R^7$, $C_1$-$C_6$alkoxy, hydroxy, $SC_1$-$C_6$alkyl, $SO_2C_1$-$C_6$alkyl, tetrazol-5-yl, $SO_2NHR^7$, $NHSO_2R^7$, $SO_3H$, $PO(OR^7)_2$, $CONR^7R^7$, CN, $NR^7R^7$, $NR^7COH$, $NR^7COC_1$-$C_6$alkyl, $NR^7CON(R^7)_2$, $NR^7COW$, $SO_2W$, or W;

$R^1$ is $C_2$-$C_{10}$alkyl, $C_3$-$C_{10}$alkenyl, $(CH_2)_{0-8}C_{3-6}$cycloalkyl, or $(CH_2)_{0-8}$phenyl unsubstituted or substituted by one to three substituents selected from $C_1$-$C_6$alkyl, nitro, Cl, Br, F, I, hydroxy, $C_1$-$C_6$alkoxy, $NR^7R^7$, $CO_2R^7$, CN, $CONR^7R^7$, W, $NR^7COH$, $NR^7COC_1$-$C_6$alkyl, $NR^7COW$, $SC_1$-$C_6$alkyl, $SO_2C_1$-$C_6$alkyl, or $SO_2W$;

$R^2$ is hydrogen, Cl, Br, F, I, CHO, hydroxymethyl, $C_1$-$C_6$alkyl, $NR^7R^7$, $CO_2R^7$, $CONR^7R^7$, $NO_2$, CN, phenyl, or W;

X is a single bond, S, or O;

$R^3$ is H, $C_{1-6}$alkyl, $C_{3-6}$alkenyl, $COC_{1-5}$alkyl, or $(CH_2)_{0-3}$phenyl;

$R^4$ is H, $C_{1-6}$alkyl, $C_{3-6}$alkenyl, or $(CH_2)_{0-3}$-phenyl;

$R^5$ is $CO_2R^7$, $CONR^7R^7$, or tetrazol-5-yl;

each n independently is 0–4;

$R^6$ is phenyl, naphthyl, 2-or 3-thienyl, 2-or 3-furyl, 2-, 3-, or 4-pyridyl, pyrimidyl, imidazolyl, thiazolyl, triazolyl, triazolyl, tetrazolyl, pyrazolyl, pyrrolyl, oxazolyl, or isoxazolyl, with each aryl or heteroaryl group being unsubstituted or substituted by $C_{1-6}$alkyl, $C_{1-6}$alkoxy, Cl, Br, F, I, $NR^7R^7$, $CO_2R^7$, $CONR^7R^7$, $SO_3H$, $SO_2NHR^7$, OH, $NO_2$, W, $SO_2C_1$-$C_6$alkyl, $SO_2W$, $SC_1$-$C_6$alkyl, $NR^7COH$, $NR^7COW$, or $NR^7COC_1$-$C_6$alkyl;

W is $C_mF_{2m+1}$, wherein m is 1–4; and each $R^7$ independently is H or $C_{1-6}$alkyl;

or a pharmaceutically acceptable salt thereof.

Compounds of formula (IV) are prepared following the methods described in European Publication Number EP 0 427 463, published May 15, 1991.

Preferred compounds included within the scope of formula (II) are:

- N-[{1-(4-carboxyphenyl)methyl]-2-n-butyl-1H-imidazol-5-yl}methyl]-β-(2-thienyl)alanine,
- N-[{1-(2-chlorophenyl)methyl]-2-n-butyl-1H-imidazol-5-yl}methyl]-β-(2-thienyl)alanine, and
- N-[{1-[(2-chlorophenyl)methyl]-2-n-butyl-1H-imidazol-5-yl}methyl]phenylalanine;

or a pharmaceutically acceptable salt thereof.

Substituted imidazoles of the formula (V) are disclosed in U.S. application Ser. No. 07/621,491, filed Nov. 30, 1990:

$$R^1-X-\underset{N}{\underset{\|}{\diagdown}}\underset{R^2}{\diagup}\overset{(CH_2)_mR}{\underset{(CH_2)_n-C-N-C-R^5}{\|}}\overset{R^3 \; R^3}{\underset{O \; R^4}{}}$$

in which:

R is adamantyl, or naphthyl, biphenyl, or phenyl, with each aryl group being unsubstituted or substituted by one to three substituents selected from halo, $C_{1-6}$alkyl, $C_{1-6}$alkoxy, OH, CN, $CO_2R^3$, tetrazol-5-yl, $SO_3H$, $SO_2NHR^3$, $NO_2$, W, $SC_{1-6}$alkyl, $SO_2C_{1-6}$alkyl, $NHSO_2R^3$, $PO(OR^3)_2$, $CONR^3R^3$, $NR^3R^3$, $NR^3COH$, $NR^3COC_{1-6}$alkyl, $NR^3CON(R^3)_2$, $NR^3COW$, or $SO_2W$;

$R^1$ is $C_{2-10}$alkyl, $C_{3-10}$alkenyl, $(CH_2)_{0-8}C_{3-6}$cycloalkyl, or $(CH_2)_{0-8}$phenyl unsubstituted or substituted by one to three substituents selected from $C_{1-6}$alkyl, $C_{1-6}$alkoxy, halo, OH, $NO_2$, $NR^3R^3$, W, $CO_2R^3$, CN, $CONR^3R^3$, $NR^3COH$, tetrazol-5-yl, $NR^3COC_{1-6}$alkyl, $NR^3COW$, $SC_{1-6}$alkyl, $SO_2W$, or $SO_2C_{1-6}$alkyl;

X is a single bond, S, $NR^3$, or O;

m is 0–4;

$R^2$ is H, $C_{1-6}$alkyl, halo, W, CHO, $CH_2OH$, $CO_2R^3$, $CONR^3R^3$, $NO_2$, CN, $NR^3R^3$, or phenyl;

each $R^3$ independently is H or $C_{1-6}$alkyl;

$R^4$ is H, $C_{1-8}$alkyl, thienyl-Y-, furyl-Y-, pyrazolyl-Y-, imidazolyl-Y-, thiazolyl-Y-, pyridyl-Y-, tetrazolyl-Y-, pyrrolyl-Y-, triazolyl-Y-, oxazolyl-Y-, isoxazolyl-Y-, or phenyl-Y-, with each aryl or heteroaryl group being unsubstituted or substituted by $C_{1-6}$alkyl, $C_{1-6}$alkoxy, halo, $NR^3R^3$, $CO_2R^3$, OH, $NO_2$, $SO_2NHR^3$, $SO_3H$, $CONR^3R^3$, W, $SO_2W$, $SC_{1-6}$alkyl, $SO_2C_{1-6}$alkyl, $NR^3COH$, $NR^3COW$, or $NR^3COC_{1-6}$alkyl;

$R^5$ is $CO_2R^3$, $CONR^3R^3$, or tetrazol-5-yl;

W is $C_qF_{2q+1}$, wherein q is 1–4;

Y is a single bond or $C_{1-6}$alkyl which is straight or branched; and n is 0–5; or a pharmaceutically acceptable salt thereof.

Compounds of formula (V) are prepared following the methods described in European Publication Number EP 0 437 103, published Jul. 17, 1991.

Preferred compounds included within the scope of formula (V) are N-[{2-n-butyl-1-(2-chlorophenyl)methyl-1H-imidazol-5-yl}methylcarbonyl]-L-phenylalanine and N-[{2-n-butyl-1-(2-chlorophenyl)methyl-1H-imidazol-5-yl}methylcarbonyl]-L-(2-thienyl)alanine; or a pharmaceutically acceptable salt thereof.

Substituted imidazoles of the formula (VI) are disclosed in Patent Cooperation Treaty Application Number WO 91/04561, filed Jun. 26, 1991:

in which:

$R^1$ is adamantyl, or phenyl, biphenyl, or naphthyl, with each aryl group being unsubstituted or substituted by one to three substituents selected from Cl, Br, F, I, $C_1$–$C_6$alkyl, nitro, $CO_2R^7$, tetrazol-5-yl, $C_1$–$C_6$alkoxy, hydroxy, $SC_1$–$C_6$alkyl, $SO_2NR^7R^7$, $NHSO_2R^7$, $SO_3H$, $CONR^7R^7$, CN, $SO_2C_1$–$C_6$alkyl, or $C_nF_{2n+1}$;

$R^2$ is $C_2$–$C_{10}$alkyl unsubstituted or substituted by $CO_2H$, OH, or $NR^7R^7$, $C_3$–$C_{10}$alkenyl, $C_3$–$C_{10}$alkynyl, $C_3$–$C_6$cycloalkyl, or $(CH_2)_{0-8}$phenyl unsubstituted or substituted by one to three substituents selected from $C_1$–$C_6$alkyl, nitro, Cl, Br, F, I, hydroxy, $C_1$–$C_6$alkoxy, $NR^7R^7$, $CO_2R^7$, CN, or $CONR^7R^7$;

X is a single bond, S, or O;

$R^3$ is hydrogen, Cl, Br, F, I, CHO, hydroxymethyl, $COOR^7$, $CONR^7R^7$, $NO_2$, or $C_nF_{2n+1}$;

each n is 1–3;

m is 0–4;

$R^4$ is $CO_2R^7$, $CONR^7R^7$, or tetrazol-5-yl;

Y is a single bond or a carbonyl group;

$R^5$ is hydrogen, $C_1$–$C_8$alkyl, $C_3$–$C_6$cycloalkyl, $(CH_2)_{0-4}$phenyl, or $(CH_2)_{0-3}$CH-diphenyl wherein each phenyl group independently is unsubstituted or substituted by one to three substituents selected from $C_1$–$C_6$alkyl, nitro, Cl, Br, F, I, hydroxy, $C_1$–$C_6$alkoxy, $NR^7R^7$, $CO_2R^7$, or $CONR^7R^7$;

$R^6$ is hydrogen or $C_1$–$C_6$alkyl; and each $R^7$ independently is hydrogen, $C_1$–$C_4$alkyl, or $(CH_2)_{0-4}$phenyl; or a pharmaceutically acceptable salt thereof.

Preferred compounds included within the scope of formula (VI) are 3-[(2-chlorophenyl)methyl]-2-propylthio-N-butrylhistidine and 3-[(2-chlorophenyl)methyl]-2-n-butyl-N-butyrylhistidine; or a pharmaceutically acceptable salt thereof.

Compounds of formula (VI) are prepared as illustrated by Example 1.

Substituted imidazoles of the formula (VII) are disclosed in Patent Cooperation Treaty Number WO 91/05391, filed Jul. 30, 1991:

in which:

$R^1$ is adamanthylmethyl, or phenyl, biphenyl, or naphthyl, with each aryl group being unsubstituted or substituted by one to three substituents selected from Cl, Br, F, I, $C_{1-6}$alkyl, nitro, $CO_2R^8$, tetrazol-5-yl, $C_{1-6}$alkoxy, hydroxy, $SC_{1-4}$alkyl, $SO_2NHR^8$, $NHSO_2R^8$, $SO_3H$, $CONR^8R^8$, CN, $SO_2C_{1-4}$alkyl, or $C_nF_{2n+1}$, wherein n is 1–3;

$R^2$ is $C_{2-10}$alkyl, $C_{3-10}$alkenyl, $C_{3-10}$alkynyl, $C_{3-6}$cycloalkyl, or $(CH_2)_{0-8}$phenyl unsubstituted or substituted by one to three substituents selected from $C_{1-6}$alkyl, nitro, Cl, Br, F, I, hydroxy, $C_{1-6}$alkoxy, $NR^8R^8$, $CO_2R^8$, CN, or $CONR^8R^8$;

X is a single bond, S, or O;

$R^3$ is hydrogen, Cl, Br, F, I, CHO, hydroxymethyl, $CO_2R^8$, $NO_2$, or $C_nF_{2n+1}$, wherein n is 1–3;

q is 0 to 4;

m is 0 to 2;

$R^4$ is H or $C_{1-6}$alkyl;

z is 0 to 1;

$R^5$ is $C_{3-6}$alkyl, $C_{3-6}$alkenyl, phenyl-Y-, 2-or 3-thienyl-Y-, 2-or 3-furyl-Y-, 2-, 3-, or 4-pyridyl-Y-, tetrazolyl-Y-, triazolyl-Y-, imidazolyl-Y-, pyrazolyl-Y-, thiazolyl-Y-, pyrrolyl-Y-, or oxazolyl-Y-, with each aryl ring being unsubstituted or substituted by $C_{1-6}$alkyl, Cl, Br, F, I, $C_{1-6}$alkoxy, $NR^8R^8$, $CO_2R^8$, or $CONR^8R^8$;

Y is a single bond or $C_{1-6}$alkyl which is branched or unbranched;

$R^6$ is $CO_2R^8$, $CONR^8R^8$, or tetrazol-5-yl;

$R^7$ is H, $CO_2R^8$, or $C_{1-6}$alkyl; and each $R^8$ independently is hydrogen, $C_{1-6}$alkyl, or $(CH_3)_{0-4}$phenyl;

or a pharmaceutically acceptable salt thereof.

A preferred compound included within the scope of formula (VII) is 3-[2-n-butyl-1-{(2-chlorophenyl)methyl}-1H-imidazol-5-yl]-2-benzylpropanoic acid or a pharmaceutically acceptable salt thereof.

Compounds of formula (VII) are prepared as illustrated by Example 2.

Substituted imidazoles of the formula (VIII) are disclosed in U.S. application Ser. No. 07/621,188, filed Nov. 30, 1990:

in which:

$R^1$ is adamantylmethyl, or phenyl, biphenyl, or naphthyl, with each aryl group being unsubstituted or substituted by one to three substituents selected from Cl, Br, F, I, $C_1$–$C_6$alkyl, nitro, $CO_2R^5$, $C_1$–$C_6$alkoxy, hydroxy, $SC_1$–$C_6$alkyl, $SO_2C_1$–$C_6$alkyl, tetrazol-5-yl, $SO_2NHR^5$, $NHSO_2R^5$, $SO_3H$, $PO(OR^5)_2$, $CONR^5R^5$, CN, $NR^5R^5$, $NR^5COH$, $NR^5COC_1$–$C_6$alkyl, $NR^5CON(R^5)_2$, $NR^5COW$, $SO_2W$, or W;

$R^2$ is $C_2$–$C_{10}$alkyl, $C_3$–$C_{10}$alkenyl, $(CH_2)_{0-8}$-$C_{3-6}$cycloalkyl, or $(CH_2)_{0-8}$phenyl unsubstituted or substituted by one to three substituents selected from $C_1$–$C_6$alkyl, nitro, Cl, Br, F, I, hydroxy, $C_1$–$C_6$alkoxy, tetrazol-5-yl, $NR^5R^5$, $CO_2R^5$, CN, $CONR^5R^5$, W, $NR^5COH$, $NR^5COC_1$–$C_6$-alkyl, $NR^5COW$, $SO_2W$, $SO_2C_1$–$C_6$alkyl, or $SC_1$–$C_6$alkyl;

X is a single bond, S, $NR^5$, or O;

n is 0–4;

$R^3$ is hydrogen, Cl, Br, F, I, CHO, hydroxymethyl, $C_1$–$C_6$alkyl, $NR^5R^5$, $CO_2R^5$, $CONR^5R^5$, $NO_2$, CN, phenyl, or W;

$R^4$ is $CO_2R^5$, $CONR^5R^5$, or tetrazol-5-yl;

Z is hydrogen, Cl, Br, F, I, $C_1$–$C_6$alkyl, $C_1$–$C_6$alkoxy, hydroxy, CN, $NO_2$, $CO_2R^5$, $COR^5R^5$, W, phenyl-Y-, naphthyl-Y-, thienyl-Y-, furyl-Y-, pyrazolyl-Y-, imidazolyl-Y-, thiazolyl-Y-, tetrazolyl-Y-, pyrrolyl-Y-, triazolyl-Y-, oxazolyl-Y-, or isoxazolyl-Y-, with each aryl or heteroaryl group being unsubstituted or substituted by $C_1$–$C_6$alkyl, $C_1$–$C_6$alkoxy, Cl, Br, F, I, $CO_2R^5$, hydroxy, $NO_2$, CN, $CONR^5R^5$, or W;

Y is a single bond or $C_1$–$C_6$alkyl, which is straight or branched;

W is $C_mF_{2m+1}$, wherein m is 1–4,; and each $R^5$ independently is H or $C_1$–$C_6$alkyl;

or a pharmaceutically acceptable salt thereof.

A preferred compound included within the scope of formula (VIII) is 3-[2-n-butyl-1-{(2-chlorophenyl)methyl}-1H-imidazol-5-yl]benzoic acid or a pharmaceutically acceptable salt thereof.

Compounds of Example (VIII) are prepared as illustrated by Example 3.

Substituted benzimidazoles of the formula (IX) are disclosed in Patent Cooperation Treaty Publication Number WO 91/16313, published Oct. 31, 1991:

in which:

$R^1$ is —C(O)NH—CH(Y)—$(CH_2)_n$-aryl, —C(O)NH—CH(Y)—$(CH_2)_n$-heteroaryl, or phenyl unsubstituted or substituted by one to three substituents selected from Cl, Br, F, I, $C_{1-6}$alkyl, $C_{1-6}$alkoxy, OH, CN, $NO_2$, $CO_2R^4$, tetrazol-5-yl, $CONR^4R^4$, $SO_3H$, $C_mF_{2m+1}$, $SC_{1-6}$alkyl, or $SO_2C_{1-6}$alkyl;

$R^2$ is hydrogen, $C_{2-10}$alkyl, $C_{3-10}$alkenyl, $C_{3-6}$-cycloalkyl, $C_mF_{2m+1}$, or $(CH_2)_{0-8}$phenyl unsubstituted or substituted by one to three substituents selected from $C_{1-6}$alkyl, $C_{1-6}$alkoxy, Cl, Br, F, I, OH, $NO_2$, $C_mF_{2m+1}$, $CO_2R^4$, or $NR^4R^4$;

$R^3$ is —$(CH_2)_n$—Y, —CH=CY—$(CH_2)_n$-aryl, —CH=CY—$(CH_2)_n$-heteroaryl, —$(CH_2)_n$—C(O)—NH—CH(Y)—$(CH_2)_n$-aryl, —$(CH_2)_n$—C(O)—NH—CH(Y)—$(CH_2)_n$heteroaryl, —$(CH_2)_m$—NH—CH(Y)—$(CH_2)_n$-aryl or —$(CH_2)_m$—NH—CH(Y)—$(CH_2)_n$-heteroaryl, when $R^1$ is an optionally substituted phenyl group; or H when $R^1$ is —C(O)NH—CH(Y)—$(CH_2)_n$-aryl or —C(O)NH—CH(Y)—$(CH_2)_n$-heteroaryl;

Y is $CO_2R^4$ or tetrazol-5-yl;

X is Cl, Br, F, I, $C_mF_{2m+1}$, $C_{1-6}$alkyl, $C_{1-6}$alkoxy, OH, O-phenyl, $CO_2R^4$, tetrazol-5-yl, CN, or $(CH_2)_{0-4}$phenyl unsubstituted or substituted by Cl, Br, F, I, $C_{1-6}$alkyl, $C_{1-6}$alkoxy, OH, $C_mF_{2m+1}$, CN, $CO_2R^4$, $NO_2$, or $NR^4R^4$;

aryl is phenyl, biphenyl, or naphthyl wherein each aryl group is unsubstituted or substituted by $C_{1-6}$alkyl, $C_{1-6}$alkoxy, Cl, Br, F, I, OH, $NO_2$, $CF_3$, $CO_2R^4$, or $NR^4R^4$;

heteroaryl is 2-or 3-thienyl, 2-, or 3-furanyl, 2-, 3-, or 4-pyridyl, pyrimidyl, imidazolyl, thiazolyl, triazolyl, or tetrazolyl wherein each heteroaryl group is unsubstituted or substituted by $C_{1-6}$alkyl, $C_{1-6}$alkoxy, Cl, Br, F, I, OH, $NO_2$, $CF_3$, $CO_2R^4$, or $NR^4R^4$;

each m independently is 1–3;

each n independently is 0–2; and each $R^4$ independently is H or $C_{1-6}$alkyl; or a pharmaceutically acceptable salt thereof.

Preferred compounds included within the scope of formula (IX) are:

5-bromo-2-n-butyl-1-(2-chlorophenyl)methyl-1H-benzimidazole-7-carboxylic acid, 2-n-butyl-1-(2-chlorophenyl)methyl-1H-benzimidazole-7-carboxylic acid, and 2-n-butyl-1-(4-carboxyphenyl)methyl-5-chloro-1H-benzimidazole-7-carboxylic acid;

or a pharmaceutically acceptable salt thereof.

Compounds of formula (IX) are prepared following the methods described in Patent Cooperation Treaty Publication Number WO 91/16313, published Oct. 31, 1991. Formula (IX) compounds are prepared as illustrated by Example 4.

The above descriptions on pages 3–18 of classes of AII receptor antagonists for use in the present invention were taken from the noted patent applications and publications. Reference should be made to such patent applications and publications for their full disclosure, the entire disclosure of each of which is incorporated herein by reference.

Also included within the scope of this invention are pharmaceutical compositions comprising a pharmaceutically acceptable carrier in association with a compound of formula (I)–(IX) and a second therapeutic agent, such as a diuretic, a calcium channel blocker, a β-adrenoceptor blocker, a renin inhibitor, or an angiotensin converting enzyme inhibitor.

This invention also relates to a method of treating hypertension by administering a compound of formula (I)–(IX) stepwise or in physical combination with a diuretic, a calcium channel blocker, a β-adrenoceptor blocker, a renin inhibitor, or an angiotensin converting enzyme inhibitor.

Most advantageously the compositions of this invention in dosage unit form are comprised of (E)-3-[2-n-butyl-1-{(4-carboxyphenyl)methyl-1H-imidazol-5-yl]-2-(2-thienyl) methyl-2-propenoic acid, or a pharmaceutically acceptable salt thereof, and a diuretic, a calcium channel blocker, a β-adrenoceptor blocker, a renin inhibitor, or an angiotensin converting enzyme inhibitor. Either can alternatively be used in the form of a non toxic salt.

Pharmaceutically acceptable acid addition salts of compounds of Formula (I)–(IX) are formed with appropriate organic or inorganic acids by methods known in the art. For example, the base is reacted with a suitable inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Representative examples of suitable acids are maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

Pharmaceutically acceptable base addition salts of compounds of Formula (I)–(IX) wherein a carboxy group is present are prepared by known methods from organic and inorganic bases, including nontoxic alkali metal and alkaline earth bases, for example, calcium, lithium, sodium, and potassium hydroxide; ammonium hydroxide, and nontoxic organic bases, such as triethylamine, butylamine, piperazine, meglumine, choline, diethanolamine, and tromethamine.

Angiotensin II antagonist activity of the compounds of Formula (I)–(IX) is assessed by in vitro and in vivo methods. In vitro antagonist activity is determined by the ability of the compounds to compete with $^{125}$I-angiotensin II for binding to vascular angiotensin II receptors and by their ability to antagonize the contractile response to angiotensin II in the isolated rabbit aorta. In vivo activity is evaluated by the efficacy of the compounds to inhibit the pressor response to exogenous angiotensin II in conscious rats and to lower blood pressure in a rat model of renin dependent hypertension.

Binding

The radioligand binding assay is a modification of a method previously described in detail (Gunther et al., *Circ. Res.* 47:278, 1980). A particular fraction from rat mesenteric arteries is incubated in Tris buffer with 80 pM of $^{125}$I-angiotensin II with or without angiotensin II antagonists for 1 hour at 25° C. The incubation is terminated by rapid filtration and receptor bound $^{125}$I-angiotensin II trapped on the filter is quantitated with a gamma counter. The potency of angiotensin II antagonists is expressed as the $IC_{50}$ which is the concentration of antagonist needed to displace 50% of the total specifically bound angiotensin II. The $IC_{50}$ of (E)-3-[2-n-butyl-1-{(4-carboxyphenyl)methyl}-1H-imidazol-5-yl}-2-(2-thienyl)methyl-2-propenoic acid is about 1.0 nM.

Aorta

The ability of the compounds to antagonize angiotensin II induced vasoconstriction is examined in the rabbit aorta. Ring segments are cut from the rabbit thoracic aorta and suspended in organ baths containing physiological salt solution. The ring segments are mounted over metal supports and attached to force displacement transducers which are connected to a recorder. Cumulative concentration response curves to angiotensin II are performed in the absence of antagonist or following a 30-minute incubation with antagonist. Antagonist disassociation constants ($K_B$) are calculated by the dose ratio method using the mean effective concentrations. The $K_B$ of (E)-3-[2-n-butyl-1-{(4-carboxyphenyl)methyl}-1H-imidazol-5-yl}-2-(2-thienyl)methyl-2-propenoic acid is about 0.20 nM.

Inhibition of pressor response to angiotensin II in conscious rats

Rats are prepared with indwelling femoral arterial and venous catheters and a stomach tube (Gellai et al., *Kidney Int.* 15:419, 1979). Two to three days following surgery the rats are placed in a restrainer and blood pressure is continuously monitored from the arterial catheter with a pressure transducer and recorded on a polygraph. The change in mean arterial pressure in response to intravenous injections of 250 mg/kg angiotensin II is compared at various time points prior to and following the administration of the compounds intravenously or orally at doses of 0.1 to 300 mg/kg. The dose of compound needed to produce 50% inhibition of the control response to angiotensin II ($IC_{50}$) is used to estimate the potency of the compounds. The $IC_{50}$ of (E)-3-[2-n-butyl-1-{(4-carboxyphenyl)methyl}-1H-imidazol-5-yl]-2-(2-thienyl)methyl-2-propenoic acid is about 0.1 mg/kg i.v. and about 5.5 mg/kg orally.

Antihypertensive activity

The antihypertensive activity of the compounds is measured by their ability to reduce mean arterial pressure in conscious rats made renin-dependent hypertensive by ligation of the left renal artery (Cangiano et al., *J. Pharmacol. Exp. Ther.* 208:310, 1979). Renal artery ligated rats are prepared with indwelling catheters as described above. Seven to eight days following renal artery ligation, the time at which plasma renin levels are highest, the conscious rats are placed in restrainers and mean arterial pressure is continuously recorded prior to and following the administration of the compounds intravenously or orally. The dose of compound needed to reduce mean arterial pressure by 30 mm Hg ($IC_{30}$) is used as an estimate of potency. The $IC_{30}$ of (E)-3-[2-n-butyl-1-{(4-carboxyphenyl)methyl}-1H-imidazol-5-yl]-2-(2-thienyl)methyl-2-propenoic acid is about 10.0 mg/kg orally.

The antihypertensive activity of the claimed pharmaceutical composition is determined using the spontaneously hypertensive rat model. The details of this in vivo test are found in Roesler, J. M., et al., *J. Pharmacol. Exp. Ther.*, 236:1–7 (1986).

BRIEF DESCRIPTION OF FIGURE

The hypotensive effects of (E)-3-[2-n-butyl-1-{(4-carboxyphenyl)methyl}-1H-imidazol-5-yl]-2-(2-thienyl)methyl}-2-propenoic acid (Compound A) before and after hydrochlorothiazide (HCTZ) administration in this test system is presented in FIG. 1. These results indicate that diuretics enhance the hypotensive efficacy of AII receptor antagonists. Thus, a combined therapy of these two classes of drugs will be likely to increase the response rate to therapy among hypertensive patients.

Figure 1:
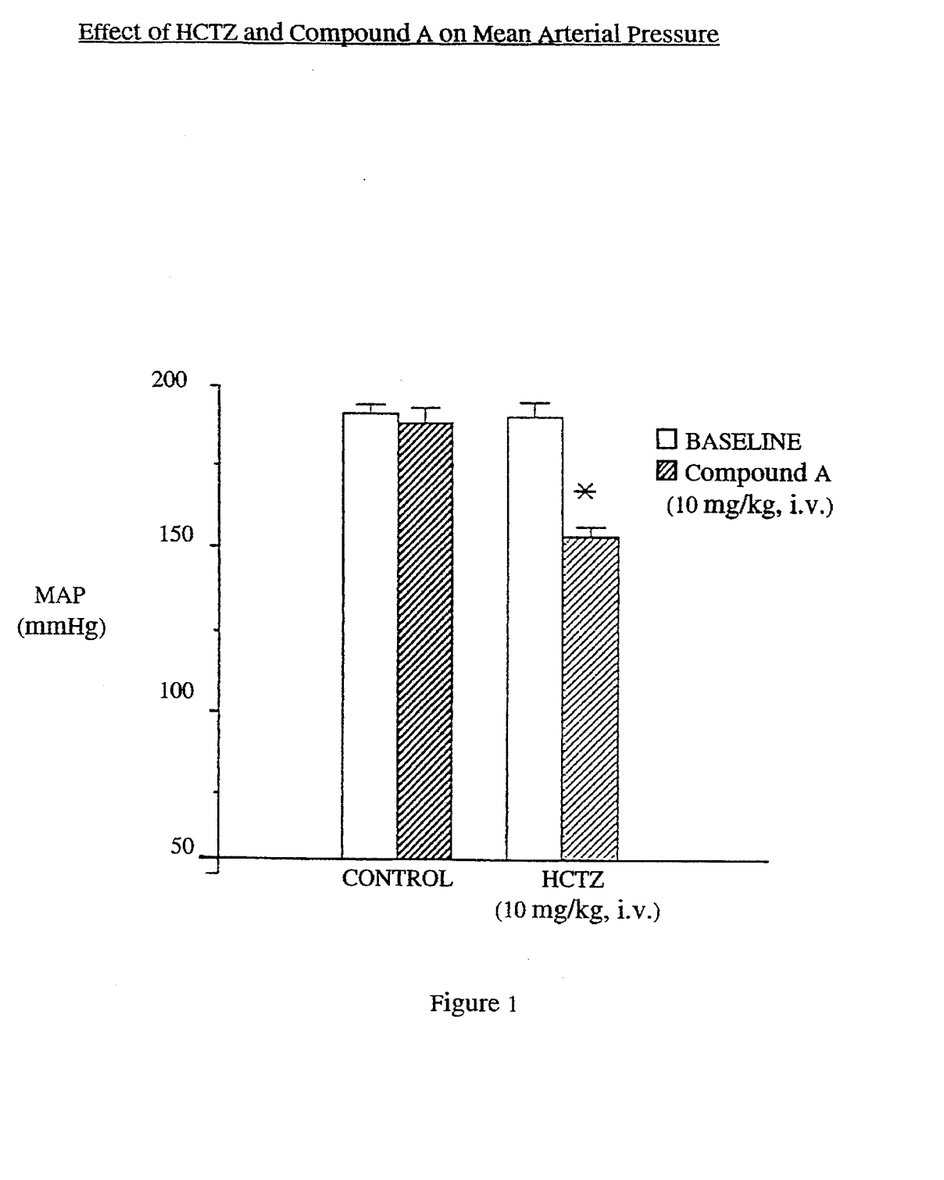

Advantageously the angiotensin II blocking compounds of formula (I)–(IX) in a preparation comprising a pharmaceutical carrier, a second therapeutic agent selected from a diuretic, a calcium channel blocker, a β-adrenoceptor blocker, a renin inhibitor, or an angiotensin converting enzyme inhibitor will be present in an amount to treat hypertension in a subject in need thereof. The preparation contains the angiotensin II blocking compound in a dosage unit in an amount from about 0.01–200 mg, preferably 1–100 mg.

The pharmaceutical carrier may be, for example, either a solid or a liquid. The administration may be parenterally, rectally, topically, transdermally or orally, the latter being the preferred route of administration. The pharmaceutical forms are, for example, syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example, polyethylene glycol, oils, or water with a suspending agent, preservative, flavouring or colouring agent.

The present invention also provides for a controlled release formulation to be administered to a mammal comprising a mixture of a micronised AII receptor antagonist and a second agent, such as a diuretic a calcium channel blocker, a β-adrenoceptor blocker, a renin inhibitor, or an angiotensin converting enzyme inhibitor, or pharmaceutically acceptable salts thereof, a water-channelling agent and a wetting agent. The mixture is in the form of a non-compressed pellet, having an enteric coat or a sustained release coat permeable to gastrointestinal juices. These slow release pharmaceutical compositions are prepared, for example, as described in U.S. Pat. No. 4,524,060, issued Jun. 18, 1985. Other controlled release formulations are described in U.S. Pat. No. 4,880,830, issued Nov. 14, 1989 and U.S. Pat. No. 5,068,112, issued Nov. 26, 1991.

The AII receptor antagonist compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydroahloride, metolazone, metoprolol tartate, methyclothiazide, methyldopa, methyldopate hydrochloride, minoxidil, pargyline hydrochloride, polythiazide, prazosin, rauwolfia serpentina, rescinnamine, reserpine, sodium nitroprusside, spironolactone, timolol maleate, trichloromethiazide, trimethophan camsylate, benzithiazide, quinethazone, ticynafan, triamterene, acetazolamide, aminophylline, cyclothiazide, ethacrynic acid, merethoxylline procaine, sodium ethacrynate, delapril hydrochloride, enalaprilat, fosinopril sodium, lisinopril, pentopril, quinapril hydrochloride, ramapril, teprotide, zofenopril calcium, diflusinal, diltiazem, felodipine, nicardipine, niludipine, minodipine, nisoldipine, nitrenedipine, verapimil and the like, as well as admixtures and combinations thereof. The AII receptor antagonist compounds of this invention can also be administered in combination with a monoamine oxidase inhibitor, such as parnate.

To illustrate these combinations, one of the angiotensin II antagonists of this invention effective clinically in the 2.5–250 milligrams per day range can be effectively combined at levels at the 0.5–250 milligrams per day range with the following compounds at the indicated per day dose range chlorothiazide (125–2000 mg), ethacrynic acid (15–200 mg), amiloride (5–20 mg), timolol maleate (5–60 mg), methyldopa (65–2000 mg), felodipine (5–60 mg) and nitrendipine (5–60 mg). In addition, triple drug combinations of hydrochlorothiazide (15–200 mg) plus amiloride (5–20 mg) plus angiotensin II antagonist of this invention (3–200 mg) or hydrochlorothiazide (15–200 mg) plus timolol maleate (5–60 mg) plus an angiotensin II antagonist of this invention (0.5–250 mg) of hydrochlorothiazide (15–200 mg) and nifedipine (5–60 mg) plus an angiotensin II antagonist of this invention (0.5–250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueious gums, celluloses, silicates or oils and the dispersion or suspension then filled into a soft gelatin capsule.

A composition for parenteral administration which can be formulated as a solution or a suspension will generally consist of a solution or suspension of the active ingredient in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository composition comprises a compound of the instant invention or a pharmaceutically acceptable salt thereof which is active when administered in th when administered in this way, with a binding and/or lubricating agent such as polymeric glycols, gelatins or coca butter or other low melting vegetable or synthetic waxes or fats.

A typical transdermal formulation comprises a conventional aqueous or non-aqueous vehicle, for example, a cream, ointment lotion or paste or in the form of a medicated plaster, patch or membrane.

For topical administration, the pharmaceutical compositions adapted include solutions, suspensions, ointments, and solid inserts. Typical pharmaceutically acceptable carriers are, for example, water, mixtures of water and water-miscible solvents such as lower alkanols or vegetable oils, and water soluble ophthalmologically acceptable non-toxic polymers, for example, cellulose derivatives such as methyl cellulose. The pharmaceutical preparation may also contain non-toxic auxiliary substances such as emulsifying, preserving, wetting, and bodying agents, as for example, polyethylene glycols; antibacterial components such as quaternary ammonium compounds; buffering ingredients such as alkali metal chloride; antioxidants such as sodium metabisulfite; and other conventional ingredients such as sorbitan monolaurate.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral, parenteral, rectal, transdermal, or topical products.

The compositions of this invention as described above are advantageously carried out in conjunction with a diuretic, particularly a thiazide diuretic, such as hydrochlorothiazide, or a loop diuretic, such as furosemide. The amount of the diuretic present in a dosage unit is from about 1 mg to about 500 mg.

Also, the compositions of this invention as described above are advantageously carried out in conjunction with a calcium channel blocker, particularly dihydropyridine calcium antagonists, such as nifedipine. The amount of the calcium channel blocker in a dosage unit is from about 5 mg to about 60 mg, preferably about 10 mg to about 30 mg.

Additionally, the compositions of this invention as described above are carried out in conjunction with a β-adrenoceptor blocker, such as propranolol. The amount of the β-adrenoceptor blocker in a dosage unit is from about 20 to about 120 mg.

Also, the compositions of this invention as described above are advantageously carried out in conjunction with a renin inhibitor, such as enalkinen. The amount of the renin inhibitor in a dosage unit is from about 10 mg to about 50 mg.

Also, the compositions of this invention as described above are advantageously carried out in conjunction with an angiotensin converting enzyme inhibitor, such as captopril or enalapril. The amount of the angiotensin converting enzyme inhibitor in a dosage unit is from about 25 to about 50 mg or form about 5 mg to about 40 mg, respectively.

The method in accordance with this invention comprises administering stepwise or in physical combination an angiotensin II receptor antagonist of formula (I)–(IX) with a second agent, such as a diuretic, a calcium channel blocker, a β-adrenoceptor blocker, a renin inhibitor, or an angiotensin converting enzyme inhibitor, in an amount sufficient to treat hypertension. The active medicament preferably will be in an amount of from about 5 mg to about 250 mg. Advantageously, equal doses, or dosage units, will be administered from one to four times daily. The total daily dosage will be from about 5 mg to about 1000 mg. When the administration described above is carried out hypotensive action is achieved in hypertensive subjects in need thereof.

The following examples are not limiting but are illustrative of the preparation of certain compounds of the invention and pharmaceutical compositions containing these compounds.

The procedure of Example 1 is illustrative of the synthesis of compounds encompassed by generic formula (IV).

EXAMPLE 1

3-[(2-Chlorophenyl)methyl]-2-propylthio-N-butyrylhistidine (i) 5-carboxymethyl-1-(2-chlorophenyl)methyl-2-thio-1H-imidazole A solution of 2-chlorobenzylamine (14.2 g, 0.1 mol) and triethylamine (13.9 mL, 0.1 mol) in dimethylformamide (100 mL) was treated with methyl chloroacetate (10.9 g, 0.1 mol). The mixture was heated at 50° C. for 3.5 hours. The cooled reaction mixture was diluted with diethyl ether, the solids filtered and the concentrated filtrate was flash chromatographed over silica gel with 6:4 hexane in ethyl acetate to provide 15.3 g (71%) of homogenous methyl 2-[N-(2-chloro-phenyl)methyl]aminoacetate. This product (15.2 g, 0.071 mol) in xylene (100 mL) was treated with 98% formic acid (2.74 mL, 0.0711 mol) and the mixture was refluxed for 2.5 hours with a Dean-Stark water separator. Evaporation gave 17.1 g (99%) of methyl 2-[N-(2-chlorophenyl)methyl-N-formyl] aminoacetate. This formylated product (17.0 g, 0.071 mol) was dissolved in methyl formate (13.3 mL, 0.216 mol) and added dropwise to a sodium methoxide mixture prepared by adding sodium metal (1.79 g, 0.0778 g-atom) to tetrahydrofuran (325 mL) followed by slow addition of methanol (3.15 mL, 0.0778 mol). The combined mixture was stirred at room temperature for 18 hours, then evaporated to dryness. This crude product was dissolved in 50% aqueous methanol (200 mL), treated with charcoal, filtered and the solution was cooled in ice. Concentrated hydrochloric acid (14.3 mL of 12N, 0.171 mol) was added slowly to this solution followed by a solution of potassium thiocyanate (8.6 g, 0.0885 mol) in water (20 mL). The mixture was heated in an oil bath held at 90° C. for 2.5 hours, then cooled to −10° C. The precipitated solid was filtered, washed with cold ethanol-water and dried at 60° C. to provide 14.7 g (74%) of 5-carboxymethyl-1-(2-chlorophenyl)methyl-2-thio-1H-imidazole; m.p. 72°–74° C.

(ii) 1-(2-chlorophenyl)methyl-5-chloromethyl-2-propylthio-1H-imidazole

A mixture of 5-carboxymethyl-1-(2-chlorophenyl)methyl-2-thio-1H-imidazole(2 g, 7.08 mmol), ethyl acetate (20 mL), 5% sodium carbonate solution (40 mL) and propylbromide (4 mL, 44 mmol) was heated at 60° C. for 18 hours. The organic layer was separated, dried over magnesium sulfate and concentrated to 2.23 g of crude product. Trituration with diethyl ether provided 1.63 g (71%) of 5-carboxymethyl-1-(2-chlorophenyl)methyl-2-propylthio-1H-imidazole; m.p. 68°–71° C. (from hexane).

The ester was hydrolyzed with aqueous sodium hydroxide solution to give 1-(2-chlorophenyl)methyl-2-thiopropyl-1H-imidazole-5-carboxylic acid; m.p. 158°–159.5° C. (from ethanol).

A solution of 5-carboxymethyl-1-1-(2-chlorophenyl)methyl-2-propylthio-1H-imidazole (3.74 g, 11.5 mmol) in dry tetrahydrofuran (50 mL) was cooled to −78° C. under argon, and a solution of diisobutyl aluminum hydride in toluene (30 mL of 1M) was added dropwise. The mixture was stirred at −78° C. for 1.5 hours, then allowed to slowly warm to room temperature. The reaction was quenched by pouring onto iced dilute acetic acid, the product was extracted into methylene chloride and the organic extracts were washed with water, 5% sodium carbonate solution and brine. The dried, concentrated product was a light tan solid (3.32 g). Crystallization from ethanol/water gave 1-(2-chlorophenyl)methyl-5-hydroxymethyl-2-propylthio-1H-imidazole; m.p. 98°–101° C.

A mixture of 1-(2-chlorophenyl)methyl-5-hydroxymethyl-2-propylthio-1H-imidazole (0.117 g, 0.393 mmol) in thionyl chloride (1 mL) was refluxed for 2 hours, evaporated in vacuo to an amorphous solid and triturated with ether to provide 1-(2-chlorophenyl)methyl-5-chloromethyl-2-propylthio-1H-imidazole hydrochloride (0.13 g, 94%).

(iii) 3-[(2-chlorophenyl)methyl]-2-propylthiohistidine ethyl ester

A solution of diisopropylamine (8.4 mL) in tetrahydrofuran (100 mL) was cooled to −78° C. under argon and a solution of n-butyl lithium (30 mL of 2.5M in hexane) was added. The mixture was stirred at −78° C. for 30 minutes and at 0° C. for 10 minutes. After being recooled to −78° C., a solution of N-(diphenylmethylene)glycine ethyl ester (Tetra. Lett., (1978), 2541, 4625) (15.4 g) in tetrahydrofuran (50 mL) was added, the mixture was stirred for 1 hour at −78° C. and a solution of 1-(2-chlorophenyl)methyl-5-chloromethyl-2-propylthio-1H-imidazole hydrochloride (9.4 g) in dry dimethylformamide (20 mL) was added. The mixture was then stirred at ambient temperature for 18 hours, poured into saturated ammonium chloride solution and the aqueous layer was extracted with methylene chloride. The organic extracts were washed with water, dried with magnesium sulfate concentrated and chromatographed over silica gel with 1% methanol in methylene chloride to afford 6.88 g of 3-[(2-chlorophenyl)methyl]-2-propylthio-N-(diphenylmethylene)histidine ethyl ester. This product (2.59 g) was dissolved in methylene chloride (52 mL), aqueous 1N hydrochloric acid solution (52 mL) was added and the mixture was stirred at 25° C. for 18 hours. The aqueous layer was separated, neutralized to pH 10.5 with sodium carbonate and the product was extracted into methylene chloride. The organic extract was dried with magnesium sulfate and concentrated to give 1.29 g (71%) of 3-[(2-chlorophenyl)methyl]-2-propylthio-histidine ethyl ester as an oil.

(iv) 3-[(2-chlorophenyl)methyl]-2-propylthio-N-butyrylhistidine ethyl ester

A solution of 3-(2-chlorophenyl)methyl-2-propylthiohistidine ethyl ester (0.4 g, 1.05 mmol) in methylene chloride (20 mL) was treated with triethylamine (0.17 mL) and butyryl chloride (0.12 mL). The mixture was stirred at 25° C. for 18 hours. The reaction was partitioned between ethyl acetate and water, and the organic layer was washed with water, dried, concentrated and chromatographed over silica gel with 1 to 3% of methanol in methylene chloride to give 0.367 g (77%) of 3-[(2-chlorophenyl)methyl]-2-propylthio-N-butyrylhistidine ethyl ester as an oil.

(v) 3-(2-chlorobenzenemethyl)-2-propylthio-N-butyrylhistidine

A mixture of 3-[(2-chlorophenyl)methyl-2-propylthio-N-butyrylhistidine ethyl ester (0.37 g, 0.819 mmole), ethanol (4 mL), water (4 mL) and potassium hydroxide pellets (0.098 g, 1.75 mmole) was stirred at 25° C. for 1 hour. The reaction was then diluted with water and the pH was adjusted to 4 with 1N aqueous hydrochloric acid solution. The product was extracted into methylene chloride, washed with water, dried and concentrated to an orange solid. Two crystallizations from chloroform provided 22 g of 3-[(2-chlorophenyl)methyl]-2-propylthio-N-butyrylhistidine; m.p. 178°–181° C.

The procedure of Example 2 is illustrative of the synthesis of compounds encompassed by generic formula (VII).

EXAMPLE 2

3-[2-n-Butyl-1-{(2-chlorophenyl)methyl}-1H-imidazol-5-yl]-2-benzylpropanoic Acid (i) 2-n-butyl-1-(2-chlorophenyl)methyl-1H-imidazole Imidazole was converted to the 1-diethoxyorthoamide derivative by the method of Curtis and Brown, *J. Org. Chem.*, (1980), 45, 20. Imidazole (12.8 g, 0.19 mol) and 118.4 g (0.8 mol) of triethylorthoformate were reacted in the presence of 1 g of p-toluenesulfonic acid to give 20.6 (61%), bp 65°–70° C. (0.1 mm) of 1-diethoxyorthoamide imidazole. This product (24.0 g, 0.14 mol) was dissolved in dry tetrahydrofuran (250 mL), cooled to −40° C. and n-butyl lithium (0.14 mol, 56.4 mL of 2.5M in hexane) was added at −40° C. to −35° C. After 15 minutes n-butyl iodide (31.1 g, 0.169 mol) was added at −40° C., and the reaction was stirred overnight at ambient temperature. The reaction was partitioned between ether and 0.3N hydrochloric acid, and the organic layer was repeatedly extracted with dilute hydrochloric acid. The combined aqueous extracts were neutralized with sodium bicarbonate solution, extracted with methylene chloride, dried over magnesium sulfate and concentrated. A flash distillation on a Kugelrohr apparatus provided 14.8 g (85%) of 2-n-butylimidazole.

2-n-Butylimidazole (9.7 g, 0.078 mol) was dissolved in methanol (50 mL) and added dropwise to a solution of sodium methoxide (from sodium hydride (2.31 g, 0.0934 mol) in methanol (250 mL)). After one hour the solution was evaporated to dryness, and the sodium salt was taken up in dry dimethylformamide (150 mL) and 2-chlorobenzyl bromide (16.3 g, 0.079 mol) was added. The mixture was heated at 50° C. for 17 hours under argon, poured onto ice water and the product was extracted into ethyl acetate. The extract was washed, dried, and concentrated to give 18.5 g of crude product which was chromatographed over silica gel with 2:1 ethyl acetate/hexane to provide 11.9 g (61%) of 2-n-butyl-1-(2-chlorophenyl)methyl-1 H-imidazole as an oil. Thin layer chromatography on silica gel with 4:1 ethyl acetate/hexane gave an $R_f$ value of 0.59.

(ii) 2-n-butyl-1-(2-chlorophenyl)methyl-5-hydroxymethyl-1H-imidazole

Method 1

A mixture of 2-n-butyl-1-(2-chlorophenyl)methyl-1H-imidazole (95.5 g, 0.384 mol), 37% formaldehyde (500 mL), sodium acetate (80 g) and acetic acid (60 mL) was heated to reflux for 40 hours under argon. The reaction was concentrated in vacuo, and the residue was stirred with 500 mL of 20% sodium hydroxide solution for 4 hours, diluted with water and extracted with methylene chloride. The extract was washed, dried, and concentrated. The crude product (117 g) was flash chromatographed over 600 g of silica gel with a gradient of ethyl acetate to 10% of methanol in ethyl acetate to give 8.3 g of starting material, 24.5 g of a mixture of starting material and product, and 44 g (41%) of 2-n-butyl-1-(2-chlorophenyl)methyl-5-hydroxymethyl-1H-imidazole; mp 86°–88° C. (from ethyl acetate). Further elution provided the bis (4,5-hydroxymethyl) derivative; mp 138°–140° C. (from ethyl acetate).

Method 2

A mixture of valeramidine methyl ether hydrochloride (250 g, 1.66 mol) and dihydroxyacetone (150 g, 0.83 mol) dissolved in liquid ammonia was allowed to stand overnight at room temperature in a pressure vessel, and then heated at 65° C. for 4 hours at 375 psi. The ammonia was allowed to evaporate, and the residue was dissolved in methanol (3 L). The resulting slurry was refluxed with added acetonitrile (1 L). The solution was decanted from the solid ammonium chloride while hot. This procedure was repeated, and the combined acetonitrile extracts were treated with charcoal, filtered hot and the filtrate was concentrated in vacuum to give the dark oil, 2-n-butyl-5-hydroxymethylimidazole (253 g, 1.63 mol, 98%).

This crude alcohol (253 g) was treated with acetic anhydride (400 mL) at −15° C. and then was allowed to warm to ambient temperature with stirring, and then stirred an additional 19 hours. The acetic anhydride was evaporated at reduced pressure, the residue taken up in methylene chloride, and the organic phase was washed with 5% sodium bicarbonate solution and water. The extract was dried over sodium sulfate and concentrated to give 323 g (83%) of 1-acetyl-4-acetoxymethyl-2-n-butylimidazole.

This diacetate was N-alkylated by the following procedure. To a solution of triflic anhydride (120 mL, 0.71 mol) in methylene chloride (200 mL) at −78° C. under argon was added a solution of diisopropyl ethylamine (128 mL, 0.73 mol) and 2-chlorobenzyl alcohol (104 g, 0.72 mol) in methylene chloride (350 mL) over a period Of 20 minutes. After being stirred an additional 20 minutes at −78° C., this solution was then treated with 1-acetyl-4-acetoxymethyl-2-n-butylimidazole (146 g, 0.61 mol) dissolved in methylene chloride (300 mL) over a 20-minute interval. The mixture was then stirred at ambient temperature for 18 hours and the solvents were evaporated, The residual 2-n-butyl-5-acetoxymethyl-1-(2-chlorophenyl)methyl-1H-imidazole was used without purification for the hydrolysis of the acetate group.

A solution of crude 2-n-butyl-5-acetoxymethyl-1-(2-chlorophenyl)methyl-1H-imidazole (250 g) in methanol (200 mL) was treated with 10% sodium hydroxide solution (700 mL) and the mixture was heated on a steam bath for 4 hours. After cooling, methylene chloride was added, the organic phase was separated, washed with water, dried and concentrated. The residue was dissolved in ether, cooled, and seeded to give the crude product. Recrystallization from ethyl acetate gave 176 g of 2-n-butyl-1-(2-chlorophenyl) methyl-5-hydroxymethyl-1 H-imidazole; mp 86°–88° C. This material was identical in all respects to the product prepared by Method 1.

(iii) 2-n-butyl-2-(2-chlorophenyl)methyl-5-chloromethyl-1H-imidazole

A mixture of 2-n-butyl-1-(2-chlorophenyl)methyl-5-hydroxymethyl-1H-imidazole, prepared in Example 1(ii), (10 g, 0.0337 mol) in thionyl chloride (75 ml) was refluxed for one hour, evaporated in vacuo and the residue azeotroped three times with toluene. The solid was triturated with ethyl ether and collected to provide 10.4 g (88%) of the hydrochloride salt of 2-n-butyl-1-(2-chlorophenyl)methyl-5-chloromethyl-1H-imidazole.

(iv) diethyl [2-n-butyl-1-{(2-chlorophenyl)methyl}-1H-imidazol-5-yl]-2-benzylmalonate To dry dimethylformamide (50 mL) under argon was added sodium hydride (0.53 g, 0.022 mol) followed by diethyl benzyl malonate (5.51 g, 0.022 mol) in dimethylformamide (10 mL) at 0° C. The mixture was stirred at ambient temperature for one hour. A solution of 2-n-butyl-1-(2-chlorophenyl)methyl-5-chloromethyl-1H-imidazole hydrochloride (3.5 g, 0.0105 mol) in dimethylformamide (40 mL) was added over 5 minutes. The reaction mixture was stirred at 25° C. for 18 hours, then partitioned between water and methylene chloride. The organic layer was washed with water, dried, and concentrated. The crude product was flash chromatographed over silica gel to give 4.54 g (85%) of the title compound as an oil.

(v) 3-[2-n-butyl-1-{(2-chlorophenyl)methyl}-1H-imidazol-5-yl]-2-benzylpropanoic acid A mixture of diethyl [2-n-butyl-1-{(2-chlorophenyl)methyl}-1H-imidazol-5-yl]methyl-2-benzylmalonate (0.72 g, 1.36 mmol), potassium hydroxide (0.83 g, 14.7 mmol), water (15 mL) and ethanol (25 mL) was refluxed for 4 hours. The ethanol was evaporated, the residual aqueous layer was extracted with diethyl ether, and the basic solution was adjusted to pH 3.75 with concentrated hydrochloric acid. The precipitated product was extracted into methylene chloride, dried, and concentrated. This crude product was flash chromatographed on silica gel with 10% methanol in methylene chloride to give 0.51 g (86%) of 3-[2-n-butyl-1-{(2-chlorophenyl)methyl}-1H-imidazol-5-yl]-2-benzylpropanoic acid; mp 118°–120° C. (from acetone/diethyl ether as the hydrochloride salt).

The procedure of Example 3 is illustrative of the synthesis of compound encompassed by generic formula (VII).

EXAMPLE 3

3-[2-n-Butyl-1-{(2-chlorophenylmethyl}-1H-imidazol-5-yl]benzoic Acid (i) 2-n-butyl-1-(trimethylsilyl)ethoxymethylimidazole Hexane-washed 80% sodium hydride (1.45 g, 0.0483 mol) in dimethylformamide (80 mL) under argon was treated with a solution of 2-n-butylimidazole (5.45 g, 0.0439 mol) in dimethylformamide (14 mL) dropwise at 25° C. and the reaction was stirred an additional hour. Then 2-(trimethylsilyl)ethoxymethyl chloride (SEM-Cl) (7.68 g, 0.0461 mol) was added, the mixture was stirred for 18 hours at ambient temperature and then partitioned between ice water and ethyl acetate. The washed, dried, concentrated organic solution was chromatographed over silica gel with 1:1 hexane in ethyl acetate to yield 10.8 g (96%) of 2-n-butyl-1-(trimethylsilyl)ethoxymethyl-imidazole.

(ii) 2-n-butyl-5-tributyltin-1-(trimethylsilyl)ethoxymethylimidazole

A solution of 2-n-butyl-1-SEM imidazole (prepared above) (6.37 g, 0.025 mol) in ethyl ether (125 mL) was treated dropwise with n-butyl lithium (0.0255 mol, 10.2 mL of 2.5M in hexane) under argon at room temperature. After being stirred for an additional 45 minutes, tributyltin chloride (8.83 g, 7.4 mL, 0.026 mol) was added dropwise. The suspension was stirred overnight, saturated ammonium chloride solution was added and the ether layer was separated, washed with brine, dried over sodium sulfate, concentrated and flash chromatographed over silica gel with 3:1 hexane/ethyl acetate to provide 11.3 g (83%) of 2-n-butyl-5-tributyltin-1-(trimethylsilyl)ethoxymethylimidazole.

(iii) methyl 3-trifluoromethanesulfonyloxy-benzoate

To a solution of methyl 3-hydroxybenzoate (1.73 g, 11.3 mmol), 4-dimethylaminopryridine (215 mg, 1.74 mmol), and 2,6-lutidine (2.0 mL, 16.6 mmol) in 60 mL of methylene chloride at −30° C. was added trifluoromethanesulfonic anhydride (2.8 mL, 16.6 mmol). After stirring the reaction mixture for 10 min at −30° C. the cooling bath was removed and the reaction was stirred at ambient temperature for 4 hours. Saturated aqueous ammonium chloride solution was then added, the layers were separated and the aqueous layer was back extracted twice with methylene chloride. The combined organic extracts were dried with sodium sulfate and the methylene chloride was removed in vacuo. The residue was dissolved in ethyl acetate and washed with water, 10% aqueous hydrochloric acid solution, saturated sodium bicarbonate solution and brine. The organic extract was dried with magnesium sulfate and the solvent was removed in vacuo. The crude product was flash chromatographed over silica gel eluting with 1:1 diethyl ether/hexane to give 3.13 (98%) of methyl 3-trifluoromethanesulfonyloxybenzoate.

(iv) methyl 3-[2-n-butyl-1-{(trimethylsilyl)ethoxymethyl}-1H-imidazol-5-yl]benzoate To a solution of 2-n-butyl-5-tributyltin-1-(trimethylsilyl)ethoxymethylimidazole (6.06 g, 11.1 mmol), methyl 3-trifluoromethanesulfonyloxybenzoate (3.13 g, 11.0 mmol) in 53 mL of 1,4-dioxane at room temperature was added tetrakis(triphenylphosphine)palladium (0) (256 mg, 0.22 mmol). The reaction mixture was stirred under argon at room temperature for 10 minutes and then 2,6-di-t-butyl-4-methylphenol (10 mg) was added. The reaction was heated at 100° C. for 3.5 hours, cooled to room temperature and treated with 70 mL of diethyl ether and 65 mL of aqueous potassium fluoride solution. The reaction mixture was left stirring at room temperature for 17 hours and then filtered through Celite®. The organic layer was washed with water and brine, dried over magnesium sulfate and concentrated in vacuo. The crude product was flash chromatographed over silica gel eluting with 3:1 ethyl acetate/hexane to give 2.88 g (67%) of methyl 3-[2-n-butyl-1-{(trimethylsilyl)ethoxymethyl}-1H-imidazol-5-yl]benzoate.

(v) methyl 3-[2-n-butyl-1-t-butoxycarbonyl-1H-imidazol-5-yl]benzoate

To a solution of methyl 3-[2-n-butyl-1-{(trimethylsilyl)ethoxymethyl}-1H-imidazol-5-yl]benzoate (2.88 g, 7.41 mmol) in 35 mL of ethanol was added 35 mL of 5N aqueous hydrochloric acid solution. The reaction mixture was heated at 55° C. for 25 hours and then an additional 20 mL of 5N aqueous hydrochloric acid solution was added. The reaction mixture was heated at 70° C. for one hour and then stirred at room temperature for 66 hours. The ethanol was removed in vacuo and the resulting aqueous layer was neutralized with saturated aqueous sodium bicarbonate solution and extracted with ethyl acetate. The organic extract was dried with sodium sulfate and the solvent was removed in vacuo.

The residue (1.46 g, 5.65 mmol) was dissolved in methanol (40 mL) and was treated with triethylamine (5.2 mL, 37.3 mmol) and di-t-butyl dicarbonate (8.4 mL, 35.4 mmol) at room temperature for 42.5 hours. The mixture was concentrated in vacuo and the crude product was flash chromatographed over silica gel with a gradient of ethyl acetate in hexane (1:8 to 4:1) to give 800 mg (30%) of methyl 3-[2-n-butyl-1-t-butoxycarbonyl-1H-imidazol-5-yl]benzoate.

(vi) methyl (3-[2-n-butyl-1-{(2-chlorophenyl)methyl}-1H-imidazol-5-yl]benzoate

To a stirred solution of trifluoromethanesulfonic anhydride (0.72 mL, 5.1 mmol) in methylene chloride (20 mL) held at −78° C. under argon was added a solution of 2-chlorobenzyl alcohol (748 mg, 5.25 mmol) and diisopropylethylamine (810 mg, 6.26 mmol) in methylene chloride (25 mL). After stirring for 15 minutes at −78° C., a solution of methyl (3-[2-n-butyl-1-t-butoxycarbonyl-1H-imidazol-5-yl]benzoate (1.53 g, 4.26 mmol) in methylene chloride (10 mL) was added dropwise over 10 minutes and the mixture was stirred overnight at room temperature. A solution of 5% sodium bicarbonate solution was added with stirring and the layers were separated, washed and dried. The reaction mixture was evaporated to dryness, the residue triturated with 1:1 hexane/ethyl acetate, the solid filtered off and the filtrate was concentrated and flash chromatographed over silica gel with 1:1 hexane/ethyl acetate to provide 600 mg (38%) of methyl (3-[2-n-butyl-1-{(2-chlorophenyl)methyl}-1H-imidazol-5-yl]benzoate.

(vii) 3-[2-n-butyl-1-{(2-chlorophenyl)methyl}-1H-imidazol-5-yl]benzoic acid

Methyl 3-[2-n-butyl-1-{(2-chlorophenyl)methyl}-1H-imidazol-5-yl]benzoic (600 mg, 1.63 mmol) was dissolved in 6 mL of ethanol and then 2 mL of 10% aqueous sodium hydroxide solution was added. The reaction mixture was stirred at room temperature overnight, 10% aqueous hydrochloric acid solution was added to pH 3.5 and the resulting solid was filtered, washed with water and dried to give 125 mg (21%) of 3-[2-n-butyl-1-{(2-chlorophenyl)methyl}-1H-imidazol-5-yl]benzoic acid as the hydrochloride salt; mp 200°–202° C.

The procedures of Example 4 is illustrative of the synthesis of compounds encompassed by generic formula (IX).

EXAMPLE 4

5-Bromo-2-n-butyl-1-(2-chlorophenyl)methyl-1H-benzimidazole-7-carboxylic Acid (i) 2,5-dibromo-3-nitrobenzoic acid The procedure described in R. K. Bentley and F. G. Holliman, *J. Chem. Soc.* (c), 2447 (1970) was used. A mixture of 2,5-dibromobenzoic acid (50 g, 0.18 mol) in concentrated sulfuric acid was vigorously stirred as fuming nitric acid (62.5 mL) was added dropwise at a rate to keep the temperature below 70° C. The reaction mixture was vigorously stirred, heated to 100° C. and then kept at 100° C. for 5 hours. The cooled reaction was cautiously poured into 2 liters of ice and vigorously stirred, the precipitate was filtered through a sintered glass funnel and the solid was washed well with water. Crystallization was achieved by dissolving the solid in acetic acid (150 mL) and after concentration to a half of the volume, crystals separated (16.72 g); mp 225°–229° C. An additional crop of 7.52 g was obtained to give a total yield of 24.24 g (41%).

(ii) 5-bromo-2-[(2-chlorophenyl)methyl]amino-3-nitrobenzoic acid

A suspension of 2,5-dibromo-3-nitrobenzoic acid (10.76 g, 0.0331 mol) in toluene (100 mL) was placed under argon, treated with 2-chlorobenzylamine (14.06 g, 0.0993 mol) and the mixture was brought to reflux. A clear, red solution resulted and the solution was refluxed for 24 hours, cooled, poured into 5% sodium hydroxide solution (600 mL) and ether (100 mL). The insoluble material was filtered off, the layers separated and the aqueous phase was added to the insoluble material and acidified with 10% hydrochloric acid solution. The separated crystalline product was collected, washed with water and the solid was crystallized from a large volume of methanol to provide 7.85 g (61.5%) of the yellow crystalline 5-bromo-2-[(2-chlorophenyl)methyl]amino-3-nitrobenzoic acid; mp 159°–161° C.

(iii) 5-bromo-2-[(2-chlorophenyl)methyl-N-valeryl]amino-3-nitrobenzoic acid

A solution of 5-bromo-2-[(2-chlorophenyl)methyl]amino-3-nitrobenzoic acid (8 g, 0.021 mmol) in pyridine (100 mL) was cooled in ice under argon and valeryl chloride (5.5 g, 0.046 mol) was added. The mixture was heated at 45° C. for 18 hours, poured into water, acidified with hydrochloric acid and the oily product was extracted into ethyl acetate. The organic extracts were washed with 10% hydrochloric acid solution and brine, and the dried, concentrated product afforded about 100% yield of the crude oil, 5-bromo-2-[(2-chlorophenyl)methyl-N-valeryl]-amino-3-nitrobenzoic acid, which was used without further purification.

(iv) 5-bromo-2-n-butyl-1-(2-chlorophenyl)methyl-1H-benzimidazole-7-carboxylic acid A solution of 5-bromo-2-[(2-chlorophenyl)methyl-N-valeryl]amino-3-nitrobenzoic acid (9.72 g, 0.0207 mol) in tetrahydrofuran (75 mL) was diluted with 5% sodium bicarbonate solution (75 mL), and then treated portionwise with sodium hydrosulfite (12 g) over 2 hours. The pH was adjusted to 7.1 with additional solid sodium bicarbonate. After an hour of stirring, 6 g of additional sodium hydrosulfite was added, and, after another hour of stirring, the mixture was filtered, diluted with ether, and the layers were separated. The organic phase was concentrated to a solid that was dissolved in acetic acid (15 mL) and concentrated hydrochloric acid (5 mL) and heated on a steam bath for 2 hours. The residual slurry was concentrated in vacuo, diluted with water and the solid was collected. The solid was dissolved in hot methanol, some insolubles filtered off, and the filtrate was concentrated to incipient crystallization. After chilling, there was obtained 4.26 g (37%) of 5-bromo-2-n-butyl-1-(2-chlorophenyl)methyl-1H-benzimidazole-7-carboxylic acid; mp 254°–255° C.

EXAMPLE 5

An oral dosage form for administering orally active formula (I)–(IX) compounds is produced by screening, mixing and filling into hard gelatin capsules the ingredients in proportions, for example, as shown below.

| Ingredients | Amounts |
| --- | --- |
| (E)-3-[2-n-butyl-1-{(4-carboxyphenyl)-methyl}-1H-imidazol-5-yl]-2-(2-thienyl)-methyl-2-propenoic acid | 100 mg |
| hydrochlorothiazide | 50 mg |
| magnesium stearate | 10 mg |
| lactose | 100 mg |

EXAMPLE 6

The sucrose calcium sulfate dihydrate and orally active formula (I)–(IX) compounds are mixed and granulated with a 10% gelatin solution. The wet granules are screened, dried, mixed with the starch, talc and stearic acid, screened and compressed into a tablet.

| Ingredients | Amounts |
| --- | --- |
| (E)-3-[2-n-butyl-1-{(4-carboxyphenyl)methyl}-1H-imidazol-5-yl]-2-(2-thienyl)methyl-2-propenoic acid | 75 mg |
| hydrochlorothiazide | 40 mg |
| calcium sulfate dihydrate | 100 mg |
| sucrose | 15 mg |
| starch | 8 mg |
| talc | 4 mg |
| stearic acid | 2 mg |

EXAMPLE 7

(E)-3-[2-n-butyl-1-{(4-carboxyphenyl)methyl}-1H-imidazol-5-yl]-2-(2-thienyl)methyl-2-propenoic acid, 50 mg, and hydrochlorothiazide, 25 mg, is dispersed in 25 ml of normal saline to prepare an injectable preparation.

EXAMPLE 8

A topical ophthamological solution for administering formula (I)–(IX) compounds is produced by mixing under sterile conditions the ingredients in proportions, for example, as shown below.

| Ingredients | Amounts (mg/ml) |
|---|---|
| (E)-3-[2-n-butyl-1-{(4-carboxy-phenyl)methyl}-1H-imidazol-5-yl]-2-(2-thienyl)-methyl-2-propenoic acid | 1.0 |
| hydrochlorothiazide | 1.0 |
| dibasic sodium phosphate | 10.4 |
| monobasic sodium phosphate | 2.4 |
| chlorobutanol | 5.0 |
| hydroxypropanol methylcellulose | 5.0 |
| sterile water | q.s. ad 1.0 mL |
| 1.0 N sodium hydroxide | q.s. ad pH 7.4 |

EXAMPLE 9

An oral dosage form for administering orally active formula (I)–(IX) compounds is produced by screening, mixing and filling into hard gelatin capsules the ingredients in proportions, for example, as shown below.

| Ingredients | Amounts |
|---|---|
| (E)-3-[2-n-butyl-1-{(4-carboxy-phenyl)methyl}-1H-imidazol-5-yl]-2-(2-thienyl)methyl-2-propenoic acid | 100 mg |
| nifedipine | 10 mg |
| magnesium stearate | 10 mg |
| lactose | 100 mg |

EXAMPLE 10

The sucrose calcium sulfate dihydrate and orally active formula (I)–(IX) compounds are mixed and granulated with a 10% gelatin solution. The wet granules are screened, dried, mixed with the starch, talc and stearic acid, screened and compressed into a tablet.

| Ingredients | Amounts |
|---|---|
| (E)-3-[2-n-butyl-1-{(4-carboxy-phenyl)methyl}-1H-imidazol-5-yl]-2-(2-thienyl)-methyl-2-propenoic acid | 75 mg |
| nifedipine | 7.5 mg |
| calcium sulfate dihydrate | 100 mg |
| sucrose | 15 mg |
| starch | 8 mg |
| talc | 4 mg |
| stearic acid | 2 mg |

EXAMPLE 11

(E)-3-[2-n-butyl-1-[(4-carboxyphenyl)methyl}-1H-imidazol-5-yl]-2-(2-thienyl)methyl-2-propenoic acid, 50 mg, and nifedipine, 5 mg, is dispersed in 25 ml of normal saline to prepare an injectable preparation.

EXAMPLE 12

An oral dosage form for administering orally active formula (I)–(IX) compounds is produced by screening, mixing and filling into hard gelatin capsules the ingredients in proportions, for example, as shown below.

| Ingredients | Amounts |
|---|---|
| (E)-3-[2-n-butyl-1-{(4-carboxy-phenyl)methyl}-1H-imidazol-5-yl]-2-(2-thienyl)-methyl-2-propenoic acid | 100 mg |
| propranolol | 100 mg |
| magnesium stearate | 10 mg |
| lactose | 100 mg |

EXAMPLE 13

The sucrose calcium sulfate dihydrate and orally active formula (I)–(IX) compounds are mixed and granulated with a 10% gelatin solution. The wet granules are screened, dried, mixed with the starch, talc and stearic acid, screened and compressed into a tablet.

| Ingredients | Amounts |
|---|---|
| (E)-3-[2-n-butyl-1-{(4-carboxy-phenyl)methyl}-1H-imidazol-5-yl]-2-(2-thienyl)-methyl-2-propenoic acid | 75 mg |
| propranolol | 75 mg |
| calcium sulfate dihydrate | 100 mg |
| sucrose | 15 mg |
| starch | 8 mg |
| talc | 4 mg |
| stearic acid | 2 mg |

EXAMPLE 14

(E)-3-[2-n-butyl-1-{(4-carboxyphenyl)methyl}-1H-imidazol-5-yl]-2-(2-thienyl)methyl-2-propenoic acid, 50 mg, and propranolol, 50 mg, is dispersed in 25 ml of normal saline to prepare an injectable preparation.

EXAMPLE 15

A topical ophthamological solution for administering formula (I)–(IX) compounds is produced by mixing under sterile conditions the ingredients in proportions, for example, as shown below.

| Ingredients | Amounts (mg/ml) |
|---|---|
| (E)-3-[2-n-butyl-1-{(4-carboxy-phenyl)methyl}-1H-imidazol-5-yl]-2-(2-thienyl)-methyl-2-propenoic acid | 1.0 |
| propranolol | 1.0 |
| dibasic sodium phosphate | 10.4 |
| monobasic sodium phosphate | 2.4 |
| chlorobutanol | 5.0 |
| hydroxypropanol methylcellulose | 5.0 |
| sterile water | q.s. ad 1.0 mL |
| 1.0 N sodium hydroxide | q.s. ad pH 7.4 |

EXAMPLE 16

An oral dosage form for administering orally active formula (I)–(IX) compounds is produced by screening, mixing and filling into hard gelatin capsules the ingredients in proportions, for example, as shown below.

| Ingredients | Amounts |
| --- | --- |
| (E)-3-[2-n-butyl-1-{(4-carboxy-phenyl)methyl}-1H-imidazol-5-yl]-2-(2-thienyl)-methyl-2-propenoic acid | 100 mg |
| enalkinen | 50 mg |
| magnesium stearate | 10 mg |
| lactose | 100 mg |

EXAMPLE 17

The sucrose calcium sulfate dihydrate and orally active formula (I)–(IX) compounds are mixed and granulated with a 10% gelatin solution. The wet granules are screened, dried, mixed with the starch, talc and stearic acid, screened and compressed into a tablet.

| Ingredients | Amounts |
| --- | --- |
| (E)-3-[2-n-butyl-1-{(4-carboxy-phenyl)methyl}-1H-imidazol-5-yl]-2-(2-thienyl)-methyl-2-propenoic acid | 75 mg |
| enalkinen | 40 mg |
| calcium sulfate dihydrate | 100 mg |
| sucrose | 15 mg |
| starch | 8 mg |
| talc | 4 mg |
| stearic acid | 2 mg |

EXAMPLE 18

(E)-3-[2-n-butyl-1-{(4-carboxyphenyl)methyl}-1H-imidazol-5-yl]-2-(2-thienyl)methyl-2-propenoic acid, 50 mg, and enalkinen, 10 mg, is dispersed in 25 ml of normal saline to prepare an injectable preparation.

EXAMPLE 19

An oral dosage form for administering orally active formula (I)–(IX) compounds is produced by screening, mixing and filling into hard gelatin capsules the ingredients in proportions, for example, as shown below.

| Ingredients | Amounts |
| --- | --- |
| (E)-3-[2-n-butyl-1-{(4-carboxyphenyl)-methyl}-1H-imidazol-5-yl]-2-(2-thienyl)-methyl-2-propenoic acid | 100 mg |
| captopril | 50 mg |
| magnesium stearate | 10 mg |
| lactose | 100 mg |

EXAMPLE 20

The sucrose calcium sulfate dihydrate and orally active formula (I)–(IX) compounds are mixed and granulated with a 10% gelatin solution. The wet granules are screened, dried, mixed with the starch, talc and stearic acid, screened and compressed into a tablet.

| Ingredients | Amounts |
| --- | --- |
| (E)-3-[2-n-butyl-1-{(4-carboxyphenyl)-methyl}-1H-imidazol-5-yl]-2-(2-thienyl)-methyl-2-propenoic acid | 75 mg |
| captopril | 40 mg |
| calcium sulfate dihydrate | 100 mg |
| sucrose | 15 mg |
| starch | 6 mg |
| talc | 4 mg |
| stearic acid | 2 mg |

EXAMPLE 21

(E)-3-[2-n-butyl-1-{(4-carboxyphenyl)methyl}-1H-imidazol-5-yl]-2-(2-thienyl)methyl-2-propenoic acid, 50 mg, and enalapril, 5 mg, is dispersed in 25 ml of normal saline to prepare an injectable preparation.

It is to be understood that the invention is not limited to the embodiments illustrated hereabove and the right to the illustrated embodiments and all modifications coming within the scope of the following claims is reserved.

What is claimed is:

1. A pharmaceutical composition comprising a diuretic, a pharmaceutically acceptable carrier and an angiotensin II receptor antagonist of the formula (I):

in which:

$R^1$ is adamantyl, phenyl, biphenyl, or naphthyl, with each aryl group being unsubstituted or substituted by one to three substituents selected from Cl, Br, F, I, $C_1$–$C_6$alkyl, nitro, A—$CO_2R^7$, tetrazol-5-yl, $C_1$–$C_6$alkoxy, hydroxy, $SC_1$–$C_6$alkyl, $SO_2NHR^7$, $NHSO_2R^7$, $SO_3H$, $CONR^7R^7$, CN, $SO_2C_1$–$C_6$alkyl, $PO(OR^7)_2$, $NR^7R^7$, $NR^7COH$, $NR^7COC_1$–$C_6$alkyl, $NR^7CON(R^7)_2$, $NR^7COW$, W, or $SO_2W$;

m is 0–4;

$R^2$ is $C_2$–$C_{10}$alkyl, $C_3$–$C_{10}$alkenyl, $C_3$–$C_{10}$alkynyl, $C_3$–$C_6$cycloalkyl, or $(CH_2)_{0-8}$phenyl unsubstituted or substituted by one to three substituents selected from $C_1$–$C_6$alkyl, nitro, Cl, Br, F, I, hydroxy, $C_1$–$C_6$alkoxy, $NR^7R^7$, $CO_2R^7$, CN, $CONR^7R^7$, W, tetrazol-5-yl, $NR^7COC_1$–$C_6$alkyl, $NR^7COW$, $SC_1$–$C_6$alkyl, $SO_2W$, or $SO_2C_1$–$C_6$alkyl;

X is a single bond, S, $NR^7$, or O;

$R^3$ is hydrogen, Cl, Br, F, I, CHO, hydroxymethyl, $COOR^7$, $CONR^7R^7$, $NO_2$, W, CN, $NR^7R^7$, or phenyl;

$R^4$ and $R^5$ are independently hydrogen, $C_1$–$C_6$alkyl, thienyl-Y-, furyl-Y-, pyrazolyl-Y-, imidazolyl-Y-, pyrrolyl-Y-, triazolyl-Y-, oxazolyl-Y-, isoxazolyl-Y-, thiazolyl-Y-, pyridyl-Y-, or tetrazolyl-Y-, except that $R^4$ and $R^5$ are not both selected from hydrogen and $C_1$–$C_6$alkyl and each heterocyclic ring is unsubstituted or substituted by $C_1$–$C_6$alkyl, $C_1$–$C_6$alkoxy, Cl, Br, F, I, $NR^7R^7$, $CO_2R^7$, $SO_2NHR^7$, $SO_3H$, or $CONR^7R^7$, OH, $NO_2$, W, $SO_2W$, $SC_1$–$C_6$alkyl, $SO_2C_1$–$C_6$alkyl, $NR^7COH$, $NR^7COW$, or $NR^7COC_1$–$C_6$alkyl;

Y is a single bond, O, S, or $C_1$–$C_6$alkyl which is straight or branched or optionally substituted by phenyl or benzyl, wherein each of the aryl groups is unsubstituted or substituted by halo, $NO_2$, $CF_3$, $C_1-C_6$alkyl, $C_1-C_6$alkoxy, CN, or $CO_2R^7$;

$R^6$ is —Z—$COOR^8$ or —Z—$CONR^7R^7$;

Z is a single bond, vinyl, —$CH_2$—O—$CH_2$—, methylene optionally substituted by $C_1-C_6$alkyl, one or two benzyl groups, thienylmethyl, or furylmethyl, or —C(O) $NHCHR^9$—, wherein $R^9$ is H, $C_1-C_6$alkyl, phenyl, benzyl, thienylmethyl, or furylmethyl;

W is $C_nF_{2n+1}$, wherein n is 1–3;

A is —$(CH_2)_m$—, —CH=CH—, —$O(CH_2)_n$—, or —$S(CH_2)_n$—;

each $R^7$ independently is hydrogen $C_1-C_6$alkyl or $(CH_2)_m$phenyl, wherein m is 0–4; and $R^8$ is hydrogen, $C_1-C_6$alkyl, or 2-di($C_1-C_6$alkyl)amino-2-oxoethyl;

or a pharmaceutically acceptable salt thereof.

2. The pharmaceutical composition of claim 1 wherein the angiotensin II receptor antagonist is (E)-3-[2-n-butyl-1-{(4-carboxyphenyl)methyl}-1H-imidazol-5-yl]-2-(2-thienyl) methyl-2-propenoic acid or a pharmaceutically acceptable salt thereof.

3. The pharmaceutical composition of claim 2 wherein the angiotensin II receptor antagonist is (E)-3-[2-n-butyl-1-{(4-carboxyphenyl)methyl}-1H-imidazol-5-yl]-2-(2-thienyl) methyl-2-propenoic acid methanesulfonate.

4. The pharmaceutical composition of claim 3 wherein the diuretic is hydrochlorothiazide or furosemide.

5. The pharmaceutical composition of claim 1 wherein the angiotensin II receptor antagonist is (E)-3-[2-n-butyl-1-{(4-carboxynapthy-1-yl)methyl}-1H-imidazol-5-yl]-2-(2-thienyl)methyl-2-propenoic acid or a pharmaceutically acceptable salt thereof.

6. The pharmaceutical composition of claim 5 wherein the diuretic is hydrochlorothiazide or furosemide.

7. A pharmaceutical composition comprising a calcium channel blocker, a pharmaceutically acceptable carrier and an angiotensin II receptor antagonist of the formula (I), as described in claim 1.

8. A pharmaceutical composition comprising a β-adrenoceptor blocker, a pharmaceutically acceptable carrier and an angiotensin II receptor antagonist of the formula (I), as described in claim 1.

9. A pharmaceutical composition comprising a renin inhibitor, a pharmaceutically acceptable carrier and an angiotensin II receptor antagonist of the formula (I), as described in claim 1.

10. A pharmaceutical composition comprising an angiotensin converting enzyme inhibitor, a pharmaceutically acceptable carrier and an angiotensin II receptor antagonist of the formula (I), as described in claim 1.

11. A method of treating hypertension which comprises administering stepwise or in physical combination a diuretic and an angiotensin II receptor antagonist of the formula (I), as described in claim 1.

12. The method of claim 11 wherein the angiotensin II receptor antagonist is (E)-3-[2-n-butyl-1-{(4-carboxyphenyl)methyl}-1H-imidazol-5-yl]-2-(2-thienyl) methyl-2-propenoic acid or a pharmaceutically acceptable salt thereof.

13. The method of claim 12 wherein the angiotensin II receptor antagonist is (E)-3-[2-n-butyl-1-{(4-carboxyphenyl)methyl}-1H-imidazol-5-yl]-2-(2-thienyl)-methyl-2-propenoic acid methanesulfonate.

14. The method of claim 13 wherein the diuretic is hydrochlorothiazide or furosemide.

15. The method of claim 11 wherein the angiotensin II receptor antagonist is (E)-3-[2-n-butyl-1-{(4-carboxynaphth-1-yl)methyl}-1H-imidazol-5-yl]-2-(2-thienyl)methyl-2-propenoic acid or a pharmaceutically acceptable salt thereof.

16. The method of claim 15 wherein the diuretic is hydrochlorothiazide or furosemide.

17. A method of treating hypertension which comprises administering stepwise or in physical combination a calcium channel blocker and an angiotensin II receptor antagonist of formula (I), as described in claim 1.

18. A method of treating hypertension which comprises administering stepwise or in physical combination a β-adrenoceptor blocker and an angiotensin II receptor antagonist of formula (I), as described in claim 1.

19. A method of treating hypertension which comprises administering stepwise or in physical combination a renin inhibitor and an angiotensin II receptor antagonist of formula (I), as described in claim 1.

20. A method of treating hypertension which comprises administering stepwise or in physical combination an angiotensin converting enzyme inhibitor and an angiotensin II receptor antagonist of formula (I), as described in claim 1.

\* \* \* \* \*